(12) United States Patent
Kitano et al.

(10) Patent No.: US 8,729,190 B2
(45) Date of Patent: May 20, 2014

(54) PARTICULAR WATER-ABSORBENT AGENT HAVING WATER-ABSORBENT RESIN AS MAIN COMPONENT

(75) Inventors: Takahiro Kitano, Himeji (JP); Takaaki Kawano, Kyotanabe (JP); Katsuyuki Wada, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 353 days.

(21) Appl. No.: 12/529,306

(22) PCT Filed: Feb. 28, 2008

(86) PCT No.: PCT/JP2008/053554
§ 371 (c)(1),
(2), (4) Date: Oct. 14, 2009

(87) PCT Pub. No.: WO2008/108277
PCT Pub. Date: Sep. 12, 2008

(65) Prior Publication Data
US 2010/0072421 A1    Mar. 25, 2010

(30) Foreign Application Priority Data

Mar. 1, 2007 (JP) ................................ 2007-051878

(51) Int. Cl.
*C08F 20/00* (2006.01)
*C08F 20/06* (2006.01)

(52) U.S. Cl.
USPC ...................... 525/329.7; 525/330.2; 428/357; 428/402; 428/403; 428/407

(58) Field of Classification Search
USPC ............ 525/329.7, 330.2; 428/357, 402, 403, 428/407
See application file for complete search history.

(56) References Cited

U.S. PATENT DOCUMENTS

| | | | |
|---|---|---|---|
| 32,649 A | 6/1861 | Rhoades | |
| 4,666,975 A | 5/1987 | Yamasaki et al. | |
| RE32,649 E * | 4/1988 | Brandt et al. | 604/368 |
| 5,382,610 A | 1/1995 | Harada et al. | |
| 5,422,405 A | 6/1995 | Dairoku et al. | |
| 5,601,542 A | 2/1997 | Melius et al. | |
| 5,672,633 A | 9/1997 | Brehm et al. | |
| 5,760,080 A | 6/1998 | Wada et al. | |
| 5,797,893 A * | 8/1998 | Wada et al. | 604/372 |
| 5,985,944 A | 11/1999 | Ishizaki et al. | |
| 6,054,541 A | 4/2000 | Wada et al. | |
| 6,060,557 A | 5/2000 | Dahmen et al. | |
| 6,087,002 A | 7/2000 | Kimura et al. | |
| 6,127,454 A | 10/2000 | Wada et al. | |
| 6,187,872 B1 * | 2/2001 | Yanase et al. | 525/330.2 |
| 6,602,950 B1 | 8/2003 | Dentler et al. | |
| 2006/0073969 A1 * | 4/2006 | Torii et al. | 502/400 |
| 2008/0280154 A1 | 11/2008 | Kobushi et al. | |

FOREIGN PATENT DOCUMENTS

| | | |
|---|---|---|
| EP | 629411 A1 | 12/1994 |
| JP | A-5-31362 | 2/1993 |
| JP | A-6-184320 | 7/1994 |
| JP | A-7-88171 | 4/1995 |
| JP | A-8-57311 | 3/1996 |
| JP | A-9-124955 | 5/1997 |
| JP | A-9-157534 | 6/1997 |
| JP | 2004-261797 | 9/2004 |
| WO | WO95/09014 | 4/1995 |
| WO | WO2006/123561 | 11/2006 |

OTHER PUBLICATIONS

International Preliminary Report on Patentability received in International Application No. PCT/JP2008/053554 dated Sep. 11, 2009.

* cited by examiner

*Primary Examiner* — Robert C Boyle
(74) *Attorney, Agent, or Firm* — Cesari and McKenna, LLP

(57) ABSTRACT

A particulate water-absorbent agent containing a polyacrylate salt-type water-absorbent resin. The agent has an absorption capacity without load of 28 g/g or higher and has a diffusion absorption index of 1.40 to 10.0 g/g min. The amount of water-soluble components in the agent, with stirring, is 15-60% by mass. The difference between this amount and the amount of water-soluble components, without stirring, is 15-50% by mass. Also disclosed is a method of making the above-identified agent.

16 Claims, 2 Drawing Sheets

PARTICULAR WATER-ABSORBENT AGENT HAVING WATER-ABSORBENT RESIN AS MAIN COMPONENT

CROSS-REFERENCE TO RELATED APPLICATIONS

This application is the National Stage of International Application No. PCT/JP2008/053554, filed on Feb. 28, 2008, which claims the benefit of Japanese Application Serial No. 2007-051878, filed on Mar. 1, 2007, the contents of both of the foregoing applications are hereby incorporated by reference in their entirety

TECHNICAL FIELD

The present invention relates to a particulate water-absorbent agent having a water-absorbent resin as a main component. More specifically, the present invention relates to a particulate water-absorbent agent having suppressed reduction of absorption capacity, after elapse of a long time, and reduced re-wet amount, a water-absorbent goods containing said particulate water-absorbent agent, and a production method for said particulate water-absorbent agent.

BACKGROUND ART

At present, as a composing material of absorbing goods such as disposable diapers, sanitary napkins, incontinence pads, a water-absorbent agent containing a water-absorbent resin as a main component, in addition to a hydrophilic fiber such as pulp, is widely used.

Such a water-absorbent resin is a water-insoluble and water-swellable cross-linked polymer, having two fundamental properties, that is, to absorb a large amount of water, and not soluble in water (amount of water-soluble component is small). In recent years, with high functionalization of absorbent goods such as disposable diapers, many improvements have been proposed. In addition, to respond to requirement for possibility to use absorbent goods over a long time (for example 16 hours at nighttime), or for making thinner, there is such tendency that concentration of a water-absorbent resin in a water-absorbent agent is increased (mass ratio of a water-absorbent resin is increased), thus importance of property of a water-absorbent resin is increasingly strengthening.

That is, as a fundamental characteristics required to a water-absorbent agent (a water-absorbent resin), it was conventionally required that amount of water-soluble component is small, and absorption capacity is high in contacting with aqueous liquid such as body fluid. However, in recent years, absorption rate, fluid permeability, strength of swollen gel, and amount of sucking to suck water from a substrate containing aqueous liquid and the like have been further required as absorbent goods. In addition, it has been similarly required that particle size distribution is very narrow, and not only absorption capacity without load but also absorption capacity under load and fluid permeability under load are high.

For example, with higher functionalization of absorbent goods, many parameter patens specifying various properties of the water-absorbent agent (water-absorbent resin) have been proposed as the following patent literature.

For example, in reissue U.S. Pat. No. 32,649, there are disclosed a water-absorbent resin excellent in absorption capacity, gel strength and water-soluble component, and an invention of a hydrogel-forming polymer composition having an amount of water-soluble component in synthetic urine after 1 hour of equal to or lower than 7.5% by mass, and an amount of water-soluble component in an equilibrium state of equal to or lower than 17% by mass. In U.S. Pat. No. 6,087,002, there is disclosed a water-absorbent resin with controlled particle size, having an amount of dissolution soluble components of equal to or lower than 1.68% by mass. In U.S. Pat. No. 5,985,944, there is disclosed a water-absorbent resin excellent in absorption capacity under load, residual monomers, water-soluble component and pore diameter of foaming. In U.S. Pat. No. 5,601,542, there is disclosed a water-absorbent resin excellent in pressure absorption capacity index (PAI) and an amount of water-soluble component of equal to or lower than 16% by mass. In U.S. Pat. No. 6,127,454, there is disclosed an invention of a water-absorbent resin having a water-soluble component for 1 minute of equal to or lower than 1% by mass, high absorption capacity under load and high absorption efficiency in an upper and lower gel layer. In U.S. Pat. No. 6,602,950, there is disclosed an invention of a water-absorbent resin excellent in absorption capacity and vertical absorption capacity under load, having a soluble component of equal to or lower than 4% by mass. In U.S. Pat. No. 6,060,557, there is disclosed a water-absorbent resin excellent in absorption capacity without load, absorption capacity under load, swelling pressure after 20 minutes, water-soluble component (from 3.5 to 10%) and maximal re-wetting amount. In U.S. Pat. No. 5,797,893, there is disclosed an invention of an absorbent agent composition having a diffusion absorption index of equal to or higher than 1.5 g/g/min., which represents maximal absorption amount per unit hour, wherein mass of a normal saline solution absorbed by the absorbent agent composition over 60 minutes is determined with time. In U.S. Pat. No. 5,760,080, there is disclosed an invention of a water-absorbent agent having a diffusion absorption capacity at 60 minutes after starting absorption, of equal to or higher than 25 g/g/min., and an amount of water-soluble component of over 0 and equal to or lower than 7% by mass. In U.S. Pat. No. 4,666,975, there is disclosed a water-absorbent resin excellent in three properties, absorption capacity, gel strength, water-soluble component, and water-absorption rate. In U.S. Pat. No. 6,187,872, there is disclosed a water-absorbent resin with low water-soluble component, which is an absorption capacity under load of equal to or higher than 20 g/g, obtained by polymerization of non-neutralized acrylic acid and then by neutralization thereof. In ERT 470. 1-99 (published in 1999), there is disclosed a measurement method for water-soluble component of a water-absorbent resin (ERT; EDNA Recommended Test), standardized by EDNA (European Disposables and Nonwovens Association), and found values of from 5.29 to 9.00% on samples A to C are described.

It should be noted that in these patent literature or non-patent literature, amount of water-soluble component is quantitatively determined by stirring water-absorbent resin particles in a large excess (from several-hundred times to several-thousand times) of water or a normal saline solution or artificial urine, extracting a water-soluble polymer from water-dispersed swollen gel particles under stirring, and by titration thereof.

It should be noted that a water-absorbent resin, which composes a water-absorbent agent which has been produced industrially in a large quantity at present, is generally produced by subjecting particles of an internally cross-linked partially neutralized polyacrylic acid-type polymer (water-absorbent resin precursor) to heat treatment in the presence of various surface cross-linking agents to introduce a cross-linked structure at the vicinity of the surface of said particles. By such surface cross-linking treatment, the water-absorbent resin precursor becomes water-insoluble and water-swelling, and is capable of exerting water-absorbing performance. In order to provide water-absorbing performance to the partially neutralized polyacrylic acid-type polymer (water-absorbent resin precursor) in this way, surface cross-linking treatment may be carried out once to the polymer. However, also technology to carry out said surface cross-linking treatment twice has been proposed.

For example, in Example 5 of the specification of the above U.S. Pat. No. 5,797,893, there is disclosed that a water-absorbent resin was obtained by subjecting a water-absorbent resin precursor to surface cross-linking treatment twice, by using a solution of a surface cross-linking agent composed of glycerine/ethylene glycol diglycidyl ether/water/ethyl alcohol. It should be noted that, in said Example, a composition of the solution of the surface cross-linking agent is the same in two times of the surface cross-linking treatment. In addition, content of water in the treatment liquid relative to mass of the polymer to be subjected to surface cross-linking treatment, is the same in two times.

Also in the pamphlet of WO 95/09014, there is disclosed technology to carry out the surface cross-linking treatment twice. Specifically, in Examples 1 to 3 of said pamphlet, the second time surface cross-linking treatment is carried out by mixing a treatment liquid containing a surface cross-linking agent to a comparative polymer and heating. It should be noted that in Example 1 of said pamphlet, content of water in the treatment liquid (relative to the polymer) is the same in the first time and the second time of the surface cross-linking treatment. In addition, in Examples 2 and 3, content of water in the treatment liquid (relative to the polymer) used in the second time is two times content of water in the treatment liquid used in the first time of the surface cross-linking treatment.

Also in the pamphlet of WO 2006/123561, there is disclosed technology to carryout surface cross-linking treatment twice (for example, claim 1). By referring to Example of said pamphlet, a precursor of water-absorbent resin particles before surface cross-linking is produced by reversed phase suspension polymerization, and content of water (moisture regain) in the precursor of the water-absorbent resin particles in the surface cross-linking treatment twice is relatively high, about 40% and about 30%, respectively, and thus it is considered that the surface cross-linking treatment is carried out always in a gel-like state.

DISCLOSURE OF THE INVENTION

As described above, there have been proposed many water-absorbent resins and parameters thereof (property control) conventionally. For example, has been proposed the improvement for enhancing absorption capacity under load or without load, reducing amount of water-soluble component, and enhancing gel strength or the like. However, any of these improvement means could not provide satisfactory properties in disposable diapers for practical use. In particular, absorption amount or rewet amount (Re-wet) of disposable diapers when used over a long time (for example 16 hours at night time), is far from satisfactory, and in view of the present increasingly higher needs for disposable diapers that can be used over a long time, it is a present state that development of means, which is capable of attaining sufficient absorbing amount even in use over a long time, is desired.

In addition, for property improvement by controlling the above various parameters, a complicated method (for example, post neutralization and low concentration polymerization, disclosed in reissue U.S. Pat. No. 32,649) is required, which raised a problem of accompanying cost increase and productivity reduction. Furthermore, there was a problem of disposal of water-absorbent resin which is used in large amounts.

The present invention was proposed in consideration of the above circumstance, and it is an object of the present invention to provide a water-absorbent agent in low cost, which is capable of providing disposable diapers durable to use over along time, and is capable of being disposed easily after use.

The present inventors have intensively studied a way to solve the above-described problems and, as a result, found surprisingly that improvement directions of a water-absorbent resin (to enhance absorption capacity under load or without load, to reduce amount of water-soluble component, to enhance gel strength and the like), which have been conventionally viewed as common sense, provide adverse effect on property of a water-absorbent agent (water-absorbent resin) used in disposable diapers on the premise of use for a long time, because of low amount of water-soluble component. And, there has been found that, in a water-absorbent agent (water-absorbent resin) for disposable diapers on the premise of use for a long time, with being different from a conventional improvement directions, amount of water-soluble component to be equal to or higher than a certain level is rather necessary for enhancement of absorption amount in use for a long time. And, it was clarified for the first time that an amount of water-soluble component under condition of stirring for certain hours (an amount of water-soluble component under stirring), which was conventionally viewed as a general index, cannot be said to be an index to evaluate practical performance (absorption characteristics in disposable diapers after elapse of long time), and practically, it is indispensable to control difference between said amount of water-soluble component under stirring and an amount of water-soluble component extracted in a standing still state without stirring (amount of water-soluble component in standing still) (i.e., amount of water-soluble component under stirring–amount of water-soluble component in standing still) into predetermined value in order to enhance absorption characteristics (absorption amount or Re-wet) in use for a long time.

Based on the above knowledge, the present inventors have found that in a water-absorbent agent having a predetermined range of diffusion absorption index and a predetermined range of absorption capacity, "an amount of water-soluble component under stirring to be equal to or higher than a certain level", which has been viewed as a non-common sense, is necessary, and still more "control of difference between the amount of water-soluble component under stirring and the amount of water-soluble component in standing still" is important, and thus completed the present invention.

That is, according to one aspect of the present invention, there is provided a particulate water-absorbent agent having a polyacrylate salt-type water-absorbent resin as a main component, and having an absorption capacity without load of equal to or higher than 28 g/g, characterized by satisfying the following (a) to (c):
(a) amount of water-soluble component under stirring is from 15 to 60% by mass;
(b) difference between an amount of water-soluble component under stirring and an amount of water-soluble component in standing still (amount of water-soluble component under stirring–amount of water-soluble component in standing still) is from 15 to 50% by mass; and
(c) diffusion absorption index is from 1.40 to 10.0 g/g/min;
wherein the amount of water-soluble component under stirring represents amount of a dissolution polymer, after 16 hours, to a normal saline solution under stirring, and the amount of water-soluble component in standing still represents amount of a dissolution polymer, after 16 hours, to a normal saline solution in standing still.

It is preferable that logarithmic standard deviation (σζ) of size distribution of the particulate water-absorbent agent provided by the present embodiment is from 0 to 0.40.

It is preferable that shape of a particle composing the particulate water-absorbent agent provided by the present embodiment is shape of a spherical primary particle or a granulated substance thereof.

In addition, it is preferable that the particulate water-absorbent agent, provided by the present embodiment, further contains a fluidity providing agent, a chelating agent, and/or water in an amount of from 0.1 to 15% by mass, relative to 100% by mass of the water-absorbent resin.

According to other embodiment of the present invention, there is provided water-absorbent goods containing the particulate water-absorbent agent and a hydrophilic fiber.

According to still more other embodiment of the present invention, there is provided a method for producing a particulate water-absorbent agent having: the polymerization step for obtaining a precursor of a polyacrylate salt-type water-absorbent resin by polymerization of an unsaturated monomer containing acrylic acid and/or a salt thereof; and the surface cross-linking step for subjecting a particle of the resultant precursor of the polyacrylate salt-type water-absorbent resin to surface cross-linking treatment, by using an aqueous solution of a surface cross-linking agent containing a surface cross-linking agent, wherein the surface cross-linking step is carried out in multiple times, and content of water (mass ratio relative to the polymer) in the aqueous solution of the surface cross-linking agent, in arbitrary consecutive two times of the surface cross-linking steps in the multiple times, is different by higher than 2 times.

Here, it is preferable that a covalent surface cross-linking agent or an ionic surface cross-linking agent is used in the surface cross-linking step.

In addition, it is preferable that content of water of the precursor of the polyacrylate salt-type water-absorbent resin in the surface cross-linking step is from 0.1 to 30% by mass relative to 100% by mass of the water-absorbent resin precursor, and content of water of the surface cross-linked water-absorbent resin precursor before further surface cross-linking treatment, is from 0.1 to 10% by mass relative to 100% by mass of the water-absorbent resin precursor.

It is preferable that the polymerization step be carried out in the presence of a dispersing agent.

In addition, it is preferable that at least either of, preferably both of the precursor of the polyacrylate salt-type water-absorbent resin and the surface cross-linked water-absorbent resin precursor, in the surface cross-linking step, satisfy the following (d) to (h):
(d) mass average particle diameter (D50) is from 200 to 600 μm;
(e) content of particles having a particle diameter of smaller than 150 μm with a JIS standard sieve, is from 0 to 5% by mass;
(f) content of particles having a particle diameter of equal to or larger than 850 μm with a JIS standard sieve, is from 0 to 5% by mass;
(g) Absorption capacity without load is equal to or higher than 28 g/g; and
(h) amount of water-soluble component under stirring is from 15 to 60 mass.

According to the water-absorbent agent of the present invention, disposable diapers, which are capable of enduring to use for a long time, can be produced in low cost. In addition, the water-absorbent agent of the present invention can be disposed easily after use.

Still more other objects, features and advantages of the present invention will become apparent with reference to the preferable embodiments exemplified in the following explanation.

DETAILED DESCRIPTION OF THE EMBODIMENT

Figure 1:
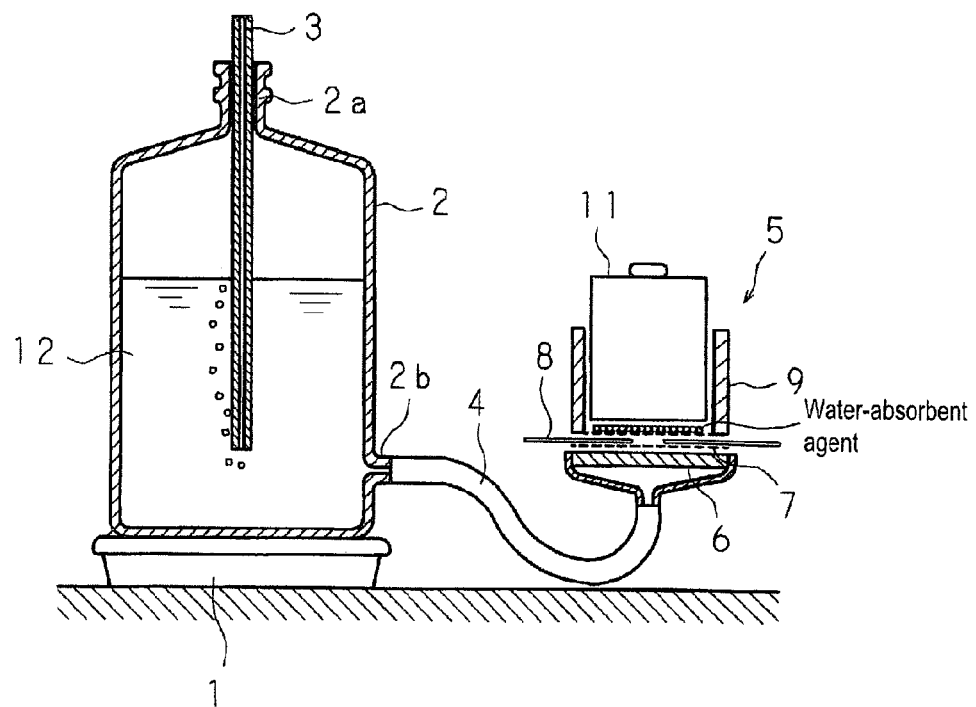
FIG. 1 is a schematic cross-sectional view showing a measurement apparatus used in measurement of diffusion absorption index of a water-absorbent agent of the present invention.

Explanation will be given below in detail on the present invention, however, it should be understood that the technical scope of the present invention should be specified based on description of the claims, and should not be limited by the following specific embodiments.

Explanation will be given below in detail on raw materials or reaction conditions or the like used in the particulate water-absorbent agent (hereinafter, it may be referred to also as simply "a water-absorbent agent") relevant to the present invention.

(1) A Water-Absorbent Agent

In the present invention, "a water-absorbent agent" means an absorbing gelling agent (other name; a fixation agent) of an aqueous liquid having a water-absorbent resin as a main component. The aqueous liquid may be water alone or a water mixture, as long as including water containing a solid, liquid or vapor, and is used for water-absorption of urine, in particular, human urine.

In addition, the water-absorbent agent of the present invention may contain other compounds, however, in view of water absorbing characteristics, a water-absorbent resin is contained in the water-absorbent agent in an amount of equal to or more than 60% by mass, preferably equal to or more than 70% by mass, still more preferably equal to or more than 80% by mass, particularly preferably equal to or more than 85% by mass, and most preferably equal to or more than 90% and if required, a chelating agent, inorganic fine particles, water or the like is still more contained as described later.

In the meantime, a "water-absorbent resin", which is a main component of the water-absorbent agent of the present invention refers to a water-absorbent resin in the form of being surface cross-linked. More specifically, a "water-absorbent resin" refers to resin particles which can absorb water and have cross-linked layer formed on the neighborhood of the surface, and the cross-linking density at the surface part of the particles is higher than that at the inner region of the particles. In the present invention, it is preferable that the water-absorbent resin is a surface cross-linked polyacrylate type water-absorbent resin and that the water-absorbent resin is a water-swellable and water-insoluble surface cross-linked particles which contains acrylic acid (salt) in the amount of preferably 30 to 100 mol %, more preferably 50 to 100 mol %, further preferably 70 to 100 mol %, and particularly preferably 90 to 100 mol % in its repeating units (excluding a cross-linking agent).

In addition, a water-absorbent region of the present invention is preferably particulate in view of water absorption characteristics, and it is preferable that its mass average particle diameter (D50) is in a range from 200 to 600 µm, more preferably in a range from 200 to 550 µm, and still more preferably in a range from 250 to 500 µm. Lower content of particles, having a size of below a JIS standard sieve 150 µm, is better, and usually the content is from 0 to 5% by mass, preferably from 0 to 3% by mass and particularly preferably from 0 to 1% by mass. Still more, lower content of particles, having a size of equal to or larger than a JIS standard sieve 850 µm, is better, and usually the content is from 0 to 5% by mass, preferably from 0 to 3% by mass and particularly preferably from 0 to 1% by mass. Bulk density thereof (specified in the specification of U.S. Pat. No. 6,562,879) is from 0.30 to 0.90 (g/cm$^3$), preferably from 0.60 to 0.80 (g/cm$^3$), and more preferably from 0.65 to 0.75 (g/cm$^3$).

Shape of a particulate water-absorbent agent is not especially limited, however, there is included spherical shape, nearly spherical shape, irregular and crushed shape (a crushed substance), bar shape, polyhedron shape, sausage shape (example; U.S. Pat. No. 4,973,632), particles with wrinkles (example; U.S. Pat. No. 5,744,564) or the like. Particle composing particulate water-absorbent agent may be primary particles (single particle), granulated particles or a mixture thereof. In addition, the particles may be a foamed porous substance. As preferable shape, a primary particle with irregular and crushed shape or shape of a granulate substance thereof is included, and as particularly preferable shape, a spherical primary particle or shape of a granulated substance thereof (for example, shape of bunch of grapes) is included.

(2) A Water-Absorbent Resin Precursor

In the present invention, a "water-absorbent resin precursor" refers to a water-absorbent resin subjected to the surface cross-linking step. Therefore, in addition to a water-absorbent resin which is not surface cross-linked, a water-absorbent resin after being subjected to at least one surface cross-linking step and before being surface cross-linked again.

An advantageous water-absorbent resin (water-absorbent resin precursor) composing a water-absorbent agent of the present invention is a polyacrylate salt-type water-absorbent resin, and is a water swellable and water-insoluble cross-linked polymer containing acrylic acid (a salt thereof) in the repeating unit (excluding a cross-linking agent) in an amount of preferably from 30 to 100% by mole, more preferably from 50 to 100% by mole, still more preferably from 70 to 100% by mole, and particularly preferably from 90 to 100% by mole.

An acid group in a repeating unit of acrylic acid or others is neutralized as a monovalent salt, preferably as an alkali metal salt or an ammonium salt, more preferably as an alkali metal salt, and particularly preferably as a sodium salt, in a range of from 0 to 100% by mole, preferably from 20 to 100% by mole, more preferably from 50 to 99% by mole, and still more preferably from 60 to 90% by mole.

As a monomer composing a repeating unit of a polyacrylate salt-type water-absorbent resin, in addition to the above acrylic acid (salt), other unsaturated monomers may be used, if required, in an amount of from 0 to 70% by mole, more preferably 0 to 50% by mole, further preferably 0 to 30% by mole, particularly preferably 0 to 10% by mole.

Specifically, hydrophilic monomers such as methacrylic acid, maleic acid (anhydride), fumaric acid, crotonic acid, itaconic acid, vinylsulfonic acid, 2-(meth)acrylamide-2-methylpropane sulfonic acid, (meth)acryloxyalkane sulfonic acid, N-vinylpyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethylene glycol(meth)acrylate, polyethylene glycol(meth)acrylate, as well as salts thereof may be used as other unsaturated monomers.

It should be noted that shape of the water-absorbent resin precursor is not especially limited, and may take arbitrary shape, for example, particle-like, granule-like, powder-like, flake-like, fiber-like shape or the like. Among these, particle-like (granule-like, powder-like) shape is preferable like the above water-absorbent resin. In addition, mass average particle diameter (D50) of the water-absorbent resin precursor is preferably from 200 to 600 µm, more preferably from 200 to 550 µm, still more preferably from 250 to 500 µm.

In the present invention, if necessary, a deodorant, an antibacterial agent, perfume, inorganic powder such as silicon dioxide and titanium dioxide, polysaccharides such as starch-cellulose and derivatives thereof, a hydrophilic polymer such as polyvinyl alcohol, thermoplastic resins such as polyethylene and polypropylene, a foaming agent, a pigment, a dye, a hydrophilic staple fiber, a plasticizer, a chain transfer agent such as hypophosphorous acid (a salt thereof) may be contained in an amount of from 0 to 5% by mass, preferably from 0 to 1% by mass, relative to the monomer.

(3) An Internal Cross-Linking Agent

As an internal cross-linking agent that may be used as an internal cross-linking agent, there are exemplified one kind or two or more kinds of a compound having at least two polymerizable double bonds in a molecule such as, for example, N,N'-methylene bisacrylamide, (poly)ethylene glycol di(meth)acrylate, (poly)propylene glycol di(meth)acrylate, (polyoxyethylene)trimethylolpropane tri(meth)acrylate, trimethylolpropane di(meth)acrylate, polyethylene glycol di(β-acryloyloxypropionate), trimethylolpropane tri(β-acryloyloxypropionate), poly(meth)allyoxyalkane; and a compound that is capable of forming a covalent bond by reaction with a carboxyl group such as polyglycidyl ether (ethylene glycol diglycidyl ether or the like), polyol (ethylene glycol, polyethylene glycol, glycerine, sorbitol or the like).

In using an internal cross-linking agent, it is preferable to use essentially a compound having at least two polymerizable double bonds in a molecule, in consideration of absorption characteristics or the like of the resultant water-absorbent resin. Used amount of the internal cross-linking agent is not especially limited, however, in view of property aspect of absorption characteristics or the like of the resultant water-absorbent resin, it is preferably used in an amount of from 0 to 5% by mole, more preferably from 0.001 to 2% by mole, relative to 100% by mole of total amount of the above-described monomer.

(4) Polymerization Step

A polymerization step is usually carried out by a solution polymerization or reversed phase suspension polymerization because of performance aspect or control easiness of polymerization. These polymerizations may be carried out even under air atmosphere, however, it is preferable to be carried out under inert gas atmosphere such as nitrogen or argon (for example, under an oxygen concentration of equal to or lower than 1%) in view of improvement of coloring too, and in addition, it is preferable that a monomer component is used after dissolved oxygen therein is sufficiently replaced with inert gas (for example, an oxygen concentration of below 1%).

Reversed phase suspension polymerization is a polymerization method, which an aqueous solution of a monomer is suspended in a hydrophobic organic solvent, and it is described in, for example, the specifications of USPs such as U.S. Pat. No. 4,093,776, U.S. Pat. No. 4,367,323, U.S. Pat. No. 4,446,261, U.S. Pat. No. 4,683,274, U.S. Pat. No. 5,244, 735. On the other hand, a solution polymerization is a method for polymerization of an aqueous solution of a monomer without using a dispersing solvent, and is described in, for example, the specifications of USPs such as U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, U.S. Pat. No. 5,380,808, or the specifications of EPs such as EP No. 0811636, EP No. 0955086, EP No. 0922717, EP No. 1178059. It should be noted that, in polymerization, monomers, cross-linking agents, polymerization initiators, and other additives described in these patents may be used also in the present invention.

It is preferable that a solvent (a polymerization solvent) composing an aqueous solution of a monomer is water or a mixture of water and a hydrophilic solvent. In addition, monomer concentration in the polymerization solvent is preferably from 20 to 80% by mass, more preferably from 25 to 70% by mass, and still more preferably from 30 to 60% by mass, and higher concentration tends to lower absorption capacity of a water-absorbent agent.

A polymerization initiator, which may be used in the polymerization step, is selected, as appropriate, depending of embodiments of polymerization. As such a polymerization initiator, there is exemplified, for example, a photodegradable-type polymerization initiator, thermal decomposition type polymerization initiator, a redox-type polymerization initiator or the like. Amount of the polymerization initiator is from 0.0001 to 1% by mole, and preferably from 0.001 to 0.5% by mole relative to 100% by mole of total amount of the monomer.

As the photodegradable-type polymerization initiator, for example, a benzoin derivative, a benzil derivative, an acetophenone derivative, a benzophenone derivative, an azo compound is exemplified. In addition, as the thermal decomposition type polymerization initiator, for example, a persulfate: sodium persulfate, potassium persulfate, ammonium persulfate; a peroxide: hydrogen peroxide, t-butyl peroxide, methyl ethyl ketone peroxide; an azo compound: an azonitrile compound, an azoamidine compound, a cyclic azoamidine compound, an azoamide compound, an alkylazo compound, 2,2'-azobis(2-amidinopropane)dihydrochloride, 2,2'-azobis [2-(2-imidazoline-2-yl)propane]dihydrochloride or the like is included. As the redox-type polymerization initiator, for example, a system of a combined use of the persulfate and a peroxide, along with a reducing compound such as L-ascorbic acid or sodium hydrogensulfite is exemplified. Or, it is also preferable to use the photodegradable-type initiator and the thermal decomposition-type polymerization initiator in combination.

(5) Reversed Phase Suspension Polymerization

As a surfactant used as a dispersing agent in reversed phase suspension polymerization, there is exemplified, for example, an anionic surfactant, a nonionic surfactant, a cationic surfactant, an amphoteric surfactant or the like.

Specifically, as the anion surfactant to be used, a fatty acid sodium salt such as mixed fatty acid sodium salt soap, sodium stearate, a higher alcohol sodium sulfate, a sodium alkyl sulfate, an alkylbenzene sulfonate is exemplified.

As the nonionic surfactant, a polyoxyethylene alkyl ether such as a polyoxyethylene higher alcohol ether, a sorbitan fatty acid ester, a glycerine fatty acid ester or the like is exemplified.

As the cationic surfactant and an amphoteric surfactant, alkylamines or an alkyl betaine or the like is exemplified.

In addition, as a dispersing agent other than a surfactant, ethyl cellulose, ethylhydroxyethyl cellulose or the like is included. Used amount of these dispersing agents may be selected, as appropriate, depending on polymerization types. Generally, it is preferably from 1 to 30% by mass, more preferably from 3 to 5% by mass, relative to 100% by mass of total monomer components composed of a polymerizable monomer and an internal cross-linking agent.

As an organic solvent used in reversed phase suspension polymerization, any one may be used as long as it is fundamentally difficult to soluble in water and inert to polymerization. As an example, there is exemplified an aliphatic hydrocarbon such as n-pentane, n-hexane, n-heptane, n-octane; an alicyclic hydrocarbon such as cyclohexane, methylcyclohexane; an aromatic hydrocarbon such as benzene, toluene, xylene. Among these, in view of stability in industrial availability, quality or the like, n-hexane, n-heptane and cyclohexane are included as preferable solvents. Used amount of these hydrophobic solvent is not especially limited, however, it is used in an amount of from 0.5 to 10 times by mass, preferably from 0.6 to 5 times by mass, relative to total amount of the aqueous solution of the monomer.

(6) A Gel Fine-Granulating Step and a Drying Step

Referring to a water-containing gel-like cross-linked polymer obtained in the above described polymerization step, it may be dried as it is, or in the case of aqueous solution polymerization, it may be dried after chipped by using a gel crushing machine or the like, if necessary. In the meantime, in the present invention, a water-containing gel-like cross-linked polymer obtained in the polymerization step itself can be used as a water-absorbent resin precursor if the gel-like polymer has a solid content of not less than a predetermined value (a water content of not more than a predetermined value) and has the above described preferable mass average particle diameter (D50) for a water-absorbent resin precursor. For example, if a water-containing gel-like cross-linked polymer has preferably not less than 60% by mass, more preferably not less than 70% by mass, and further preferably not less than 80% by mass, it can be used as a water-absorbent resin precursor. In the meantime, the particle diameter or a solid content of the water-containing gel-like cross-linked polymer is outside the above described range, a desirable surface cross-linked layer is difficult to be formed in the surface cross-linking step.

The chipping water-containing gel-like cross-linked polymer may be carried out by various methods and there is exemplified, for example, a method for crushing by extrusion from a screw-type extruder having a porous structure with arbitrary shape.

Drying temperature suitably used in the present invention is not especially limited, however, drying is carried out, for example, in a range of from 50 to 300° C. (in the case of equal to or lower than 100° C., execution of azeotropic dehydration or execution under reduced pressure is preferable), preferably from 100 to 250° C. and more preferably from 150 to 200° C. to enhance absorption capacity.

As a drying method, various methods may be adopted including heating drying, hot-air drying, drying under reduced pressure, fluid bed drying, infrared ray drying, microwave drying, drum drier drying, dehydration by an azeotrope with a hydrophobic organic solvent, drying at high humidity using high temperature steam and the like. As a preferable embodiment, contact drying with vapor having a dew point of from 40 to 100° C., more preferably from 50 to 90° C. is exemplified.

The water-containing gel-like cross-linked polymer obtained during a polymerization reaction or after completion of the polymerization reaction by aqueous solution polymerization, may be subjected to crushing and drying, by a predetermined method, to a fragment having a size of about 0.1 mm to about 50 mm, still more from 0.2 to 10 mm, more preferably from about 0.5 to about 5 mm. Drying temperature is not especially limited, however, it may be set, for example, within a range of from 100 to 250° C., more preferably within a range of from 120 to 200° C. In addition, drying time may be determined, as appropriate, and not especially limited, however, from about 10 seconds to 5 hours, and still more from about 1 minute to about 2 hours are suitable.

By the above drying treatment, dry substance of water-containing gel-like cross-linked polymer (hereinafter, referred to simply as "dry substance") which solid content is preferably from 80 to 100% by mass, more preferably from 90 to 97% by mass is obtained.

In addition, the water-containing gel-like cross-linked polymer obtained by reversed phase suspension polymerization, during a polymerization reaction or after completion of the polymerization reaction, may be separated from an organic solvent by decantation or evaporation, for example, after azeotropic dehydration in a dispersed state in the organic solvent such as, for example, a hydrocarbon, to a solid content of equal to or higher than 60% by mass, preferably equal to or higher than 70% by mass, and subjected to further drying, if necessary.

As a drying method, various methods may be adopted including heating drying, hot-air drying, drying under reduced pressure, infrared ray drying, microwave drying, drum drier drying, dehydration by an azeotrope with a hydrophobic organic solvent, drying at high humidity using high temperature steam and the like, and not especially limited.

It should be noted that the above drying treatment may be carried out at the same time as polymerization or after polymerization step to make an adjustment finally within the above range of solid content.

A dry substance is obtained by the above drying treatment.
(7) A Crushing or a Classification Step A dry substance obtained by drying may be subjected to the crushing or the classification step for particle diameter control, corresponding to objectives, if necessary. Referring to these methods, there are described, for example, in the pamphlet of WO 2004/69915.

By the step mentioned above, particulate resin particles which are not surface cross-linked and have a predetermined particle diameter range and an above described preferable mass average particle diameter (D50) are obtained. The resin particles can be used as a water-absorbent resin precursor.
(8) Property Before Surface Cross-Linking By setting polymerization conditions (amount of a cross-linking agent, polymerization concentration, drying temperature and the like) in obtaining the water-absorbent resin precursor, as appropriate, absorption capacity or amount of water-soluble component of the resultant water-absorbent resin precursor can be controlled. Absorption capacity of the water-absorbent resin precursor is preferably equal to or higher than 28 g/g, more preferably in a range of from 30 to 60 g/g and still more preferably from 35 to 50 g/g.

In addition, in the present invention, contrarily to a conventional common sense, a water-absorbent resin having a high amount of water-soluble component under stirring is used. Therefore, the amount of water-soluble component under stirring is preferably from 15 to 60% by mass, more preferably from 18 to 60% by mass, still more preferably from 20 to 60% by mass, and particularly preferably from 22 to 50% by mass. The low amount of water-soluble component is not capable of providing the water-absorbent agent of the present invention; on the other hand, the too high amount of water-soluble component may provide inferior durability or the like in some cases.

Preferable examples of a method for obtaining a water-absorbent resin precursor in which an absorption capacity and an amount of water-soluble component under stirring in the above described preferable (relatively high) range are the following (i) to (iii), for example.

(i) polymerizing with the monomer concentration in the range of 30 to 80% by mass (i.e., relatively high concentration) and the amount of a internal cross-linking agent of 0 to 0.05% by mole (i.e., relatively low amount);

(ii) polymerizing with the monomer concentration in the range of less than 30% by mass (i.e., relatively low concentration) and the amount of a internal cross-linking agent of 0.1 to 5% by mole (i.e., relatively high amount) and drying at a temperature in the range of 200 to 300° C. (i.e., relatively high temperature);

(iii) a monomer containing a chain transfer agent in the amount of not more than 5% by mass in the method of (i) or (ii) above (for example, U.S. Pat. No. 5,185,413, U.S. Pat. No. 6,335,406).
(9) Surface Cross-Linking A water-absorbent resin composing the water-absorbent agent of the present invention can be obtained by subjecting the water-absorbent resin precursor particles obtained in the above to surface cross-linking in the presence of a surface cross-linking agent.

As a suitable surface cross-linking agent, for example, one kind or two or more kinds of the following are included: an oxazoline compound (U.S. Pat. No. 6,297,319), a vinyl ether compound (U.S. Pat. No. 6,372,852), an epoxy compound (U.S. Pat. No. 625,488), an oxetane compound (U.S. Pat. No. 6,809,158), a polyhydric alcohol compound (U.S. Pat. No. 4,734,478), a polyamide polyamine-epihalo adduct (U.S. Pat. No. 4,755,562 and U.S. Pat. No. 4,824,901), a hydroxyacrylamide compound (U.S. Pat. No. 6,239,230), an oxazolidinone compound (U.S. Pat. No. 6,559,239), a bis or poly-oxazolidinone compound (U.S. Pat. No. 6,472,478), a 2-oxotetrahydro-1,3-oxazolidine compound (U.S. Pat. No. 6,657,015), an alkylene carbonate (U.S. Pat. No. 5,672,633) or the like. In addition, into these surface cross-linking agents, an aqueous cation such as an aluminum salt (U.S. Pat. No. 6,605,673 and U.S. Pat. No. 6,620,899), an alkaline metal salt (USP 2004/106745), an organic acid and an inorganic acid (U.S. Pat. No. 5,610,208) or the like may be used in combination. In addition, it may be adopted that the water-absorbent resin precursor is surface cross-linked using active energy ray such as UV (U.S. Pat. No. 7,201,941), or polymerization of a monomer is carried out on the surface of a water-absorbent resin, and then surface cross-linking (USP 2005/48221) is carried out.

Among these, a polyhydric alcohol compound, a polyvalent epoxy compound, a polyvalent amine compound or a salt thereof, an alkylene carbonate compound, multivalent metal salt are preferably used.

As a surface cross-linking agent, for example, a covalent cross-linking agent, which forms covalent bond with carboxyl group within a water-absorbent resin precursor by dehydration reaction or addition reaction by heating, is included. In particular, there is included, for example, a polyhydric alcohol compound, organic surface cross-linking agent such as (di, tri, tetra, poly) ethylene glycol, (di, poly) propylene glycol, 1,3-propanediol, 2,2,4-trimethyl-1,3-pentanediol, (poly)glycerine, 2-butene-1,4-diol, 1,4-butanediol, 1,3-butanediol, 1,5-pentanediol, 1,6-hexanediol, trimethylol propane, di or triethanol amine, pentaerythritol, sorbitol; an epoxy compound such as (poly)ethylene glycol diglycidyl ether, (di, poly)glycerol polyglycidyl ether, (di,poly)propylene glycol diglycidyl ether, glycidol or the like; a polyvalent oxazoline compound such as 1,2-ethylene bis oxazoline or the like; an alkylene carbonate such as 1,3-dioxolane-2-one or the like.

In addition, an ionic surface cross-linking agent, which forms an ionic bond by a salt exchange with a carboxyl group in a water-absorbent resin precursor, can be also used as a surface cross-linking agent. Specifically, aluminum sulfate, calcium sulfate, aluminum chloride, magnesium chloride, calcium chloride, zirconium oxide chloride octahydrate, ammonium zirconium carbonate, potassium zirconium carbonate, sodium zirconium carbonate, zirconium sulfate hydrate, zirconium acetate, zirconium nitrate, zirconium hydroxy chloride, titanium triethanol aminate, titanium lactate and so on, each of which is an inorganic surface cross-linking agent (an inorganic ionic surface cross-linking agent), are exemplified.

Further, polyvalent amine compounds such as polyallylamine and polyvinylamine etc. and organic polymeric polycations (preferably having weight average molecular weight of not less than 2000) such as polyethyleneimine can be also used as a surface cross-linking agent in the present invention. In the organic polymeric polycation is used as a surface cross-linking agent, either polyvalent surface cross-linking or ionic surface cross-linking is appropriately selected depending on the below described temperature for the surface cross-linking.

As amount of a surface cross-linking agent, it is preferable to use from 0.01 to 10% by mass, and more preferably from 0.5 to 5% by mass, relative to 100% by mass of the water-absorbent resin precursor. The amount of the surface cross-linking agent less than 0.01% by mass may lower fluid permeability. Use of the surface cross-linking agent in the amount of over 10% by mass may extremely lower absorption capacity in some cases.

(10) An Example of a Preferable Surface Cross-Linking Method

Other embodiment of the present invention relates to a preferable production method for obtaining the water-absorbent agent of the present invention. However, the water-absorbent agent of the present invention should not be limited to one produced by this production method. That is, the present invention provides a method for producing a particulate water-absorbent agent having:
the polymerization step for obtaining a precursor of a polyacrylate salt-type water-absorbent resin by polymerizing an unsaturated monomer containing acrylic acid and/or a salt thereof; and
the surface cross-linking step for subjecting a particle of the resultant precursor of the polyacrylate salt-type water-absorbent resin to surface cross-linking treatment by using an aqueous solution of a surface cross-linking agent, containing a surface cross-linking agent,
wherein the surface cross-linking step is carried out in multiple times, and content of water (mass ratio relative to the polymer) in the aqueous solution of the surface cross-linking agent, in arbitrary consecutive two times of the surface cross-linking steps in the multiple times, is different by higher than 2 times.

In the production method of the present embodiment, the surface cross-linking step is carried out in multiple times. Times of the surface cross-linking step is not especially limited as long as it is multiple times, however, in consideration of the effect of the present invention to equipment cost, it is preferably from two to five times, more preferably from two to three times and particularly preferably two times. Here, in the multiple times of the surface cross-linking steps, surface cross-linking agents to be used may be each the same or different. The surface cross-linking step is carried out specifically, by the addition of a surface cross-linking agent to a water-absorbent resin precursor not surface cross-linked yet, or a surface cross-linked water-absorbent resin precursor (a water-absorbent resin precursor after being subjected to surface cross-linking treatment once or more; hereinafter may be referred to simply as "a water-absorbent resin precursor"), and by heating thereof.

According to a production method of the present embodiment, by repeating the above-described surface cross-linking step in multiple times, it becomes possible for a surface cross-linked layer, having higher cross-linking density as compared with the inner part, to be present, in suitable thickness, at the surface of the polymer particles over a wide range. As a result, lowering of absorption capacity of the finally obtained water-absorbent agent, after elapse of a long time, is suppressed, and Re-wet is reduced. It should be noted that in the case where total amount of the surface cross-linking agent to be added in the multiple times of the surface cross-linking steps, is added in one time, by execution of the surface cross-linking step once, it raises a problem such as a surface cross-linked layer becomes partially thick.

In addition, it may be adopted a method for heating after mixing in portions in two times in the surface cross-linking agent addition step, however, repeating of the addition and the heating steps is necessary to obtain the effect of the present invention.

In the heating step in the surface cross-linking, the temperature of the powder of the water-absorbent resin precursor is controlled preferably in the range of 80 to 300° C., more preferably in the range of 120 to 250° C., further preferably in the range of 150 to 230° C. in view of the absorption capacity in the case when a covalent (organic) surface cross-linking agent is used.

In addition, the temperature of the powder of the water-absorbent resin precursor is controlled preferably in the range of 40 to 120° C., more preferably in the range of 50 to 100° C., further preferably in the range of 50 to 80° C. in view of the absorption capacity in the case when an ionic (inorganic) surface cross-linking agent is used in the heating step in the surface cross-linking of the present invention.

In the production method of the present embodiment, content of water in the aqueous solution of the surface cross-linking agent used in arbitrary consecutive two times of the surface cross-linking steps, among the multiple times of the surface cross-linking steps, is different by higher than 2 times, preferably higher than 2 times and not more than 6 times, more preferably from 2.5 to 5.5 times, still more preferably from 3 to 5.5 times, particularly preferably from 3 to 5 times. Here, content of water in the aqueous solution of the surface cross-linking agent is value determined as mass ratio relative to a polymer to be treated with the aqueous solution of the surface cross-linking agent (a water-absorbent resin precursor). It is considered that, by setting, in this way, content of water in treatment liquids to be different by higher than 2 times, a multi-layer-like surface cross-linked layer, having both a surface cross-linked layer with thin thickness and high density, and a surface cross-linked layer with thick thickness and low density, is formed, by which a water-absorbent agent, which suppresses lowering of absorption capacity after elapse of a long time, and has excellent gel layer diffusion performance as well.

In the meantime, it is not preferable that an ionic surface cross-linking agent such as polyvalent metal compounds is used for the first cross-linking step. This is because such use of the ionic surface cross-linking agent causes cross-linking with metal ions with high density on the surface of the water-absorbent resin presursor.

Among the above described consecutive two or more times of surface cross-linking steps, water content of any step may be higher than other step(s). For example, in the case when two surface cross-linking steps are carried out, if the amount of water in the aqueous solution of a surface cross-linking agent used in one surface cross-linking step (with less water content) is 0.1% by mass relative to 100% by mass of the water-absorbent resin precursor, the amount of water in the aqueous solution of a surface cross-linking agent used in the other surface cross-linking step (with more water content) may be not less than 0.2% by mass (preferably in the range of 0.2 to 0.6% by mass) relative to 100% by mass of the water-absorbent resin precursor.

The absolute amount of water in an aqueous solution of a surface cross-linking agent is not especially limited, but the amount of water in the aqueous solution of a surface cross-linking agent used in one surface cross-linking step (with less water content) is preferably in the range of 0.1 to 3% by mass, more preferably in the range of 0.1 to 2% by mass, further preferably in the range of 0.3 to 1% by mass relative to 100% by mass of the water-absorbent resin precursor. In addition, the amount of water in the aqueous solution of a surface cross-linking agent used in the other surface cross-linking step (with more water content) is preferably in the range of 0.5 to 7% by mass, more preferably in the range of 0.5 to 5% by mass relative to 100% by mass of the water-absorbent resin precursor.

Moreover, in embodiments in which three or more surface cross-linking steps are carried out, it is preferable to control the water content in an aqueous solution of a surface cross-linking agent for the first two surface cross-linking steps. In this case, the water content in an aqueous solution of a surface cross-linking agent used in the third or later surface cross-linking step(s) is not especially limited, but is preferably in the range of 0.01 to 1% by mass, more preferably in the range of 0.05 to 1% by mass, further preferably in the range of 0.1 to 1% by mass relative to 100% by mass of the water-absorbent resin precursor.

It should be noted that technology to carry out two times of surface cross-linking treatment to a water-absorbent resin is disclosed in the specification of U.S. Pat. No. 5,797,893 or U.S. Pat. No. 5,672,633. However, in such conventional technology, there is no disclosure on change of amount of water or an amount of water-soluble component, and the water-absorbent resin of the present invention cannot be obtained.

Still more, total amount of water used in the heating cross-linking steps to be carried out in multiple times is preferably from 1 to 10% by mass, and most preferably from 1 to 5% by mass, relative to 100% by mass of the water-absorbent resin precursor. In the case where the total amount of water is from 1 to 10% by mass relative to 100% by mass of the water-absorbent resin precursor, the aqueous solution of the surface cross-linking agent is sufficiently infiltrated into the surface of a water-absorbent resin, which is capable of forming a multi-layer-like surface cross-linked layer having suitable thickness and density.

In addition, in another preferred embodiment, a covalent (organic) surface cross-linking agent such as polyvalent alcohol compounds and polyvalent epoxy compounds is used for at least one surface cross-linking step, and an ionic (inorganic) surface cross-linking agent such as polyvalent metal compounds for at least another one surface cross-linking step. More preferably, a covalent (organic) surface cross-linking agent is used for the first or a halfway cross-linking step(s) (in other words, other than the last cross-linking step) and an ionic (inorganic) surface cross-linking agent is used for the last surface cross-linking step, among a plurality of surface cross-linking steps. By such embodiments, the permeability of a gel layer can be improved.

In addition, in the production method of the present embodiment, in view of excellent gel layer diffusion, content of water of the water-absorbent resin precursor to be subjected to the first time of the surface cross-linking treatment, in the surface cross-linking steps, is preferably from 0.1 to 30% by mass, more preferably from 1 to 20% by mass, and still more preferably from 1 to 10% by mass, relative to 100% by mass of the water-absorbent resin precursor. In addition, content of water of the water-absorbent resin precursor to be subjected to the second time or more of the surface cross-linking treatment, is preferably a little lower level, and preferably from 0.1 to 10% by mass, more preferably from 0.1 to 5% by mass, and still more preferably from 0.1 to 3% by mass, relative to total amount of the water-absorbent resin precursor.

Interval between the multiple times of the surface cross-linking steps is not especially limited, however, it is preferable that the subsequent surface cross-linking step is carried out, after completing a certain time of the surface cross-linking step (heating step), within from 0.01 to 10 minutes, more preferably within from 0.5 to 5 minutes, and still more preferably within from 1 to 3 minutes. According to such an embodiment, there are advantages that temperature of the water-absorbent resin precursor to be subjected to the subsequent surface cross-linking treatment is not lowered, and infiltration of the water-absorbent resin precursor into the inside of the surface and handling are good.

It should be noted that, in obtaining the water-absorbent agent of the present invention, at least either of, preferably both of the water-absorbent resin precursor and the water-absorbent resin precursor satisfy the following (d) to (h):

(d) mass average particle diameter (D50) is from 200 to 600 μm;

(e) content of particles, having a particle diameter of smaller than 150 μm with a JIS standard sieve, is from 0 to 5% by mass;

(f) content of particles, having a particle diameter of equal to or larger than 850 μm with a JIS standard sieve, is from 0 to 5% by mass;

(g) Absorption capacity without load is equal to or higher than 28 g/g; and (h) amount of water-soluble component under stirring is from 15 to 60 mass.

In mixing the water-absorbent resin and the surface cross-linking agent, a hydrophilic organic solvent may be used as a solvent, if necessary. As said hydrophilic organic solvent, there is included, for example, lower alcohols such as methyl alcohol, ethyl alcohol, n-propyl alcohol, isopropyl alcohol, n-butyl alcohol, isobutyl alcohol t-butyl alcohol; ketones such as acetone; ethers such as dioxane, tetrahydrofuran, alkoxypolyethylene glycol; amides such as N,N-dimethylformamide; sulfoxides such as dimethyl sulfoxide. Used amount of the hydrophilic organic solvent depends on kind or particle diameter or the like of a water-absorbent resin, however, it is preferable to be equal to or lower than 20% by mass, more preferably from 0.1 to 10% by mass, relative to 100% by mass of the water-absorbent resin precursor or a water-absorbent resin precursor to be subjected to the surface cross-linking treatment.

And, a method for mixing the water-absorbent resin precursor and the surface cross-linking agent is not especially limited, however, such a method is preferable for mixing the surface cross-linking agent dissolved in water and/or a hydrophilic organic solvent, directly, spraying or dropping, onto a substance to be treated.

A mixing apparatus used in mixing the water-absorbent resin precursor and the surface cross-linking agent has preferably strong mixing force, to uniformly and surely mix both. As the mixing apparatus, for example, a cylinder-type mixer, a double wall cone-type mixer, a V-character-type mixer, a ribbon-type mixer, a screw-type mixer, a fluid-type furnace rotary disk-type mixer, an air flow-type mixer, a double arm-type kneader, an internal mixer, a crushing-type kneader, a rotation-type mixer, a screw-type extruder, a turbulizer or the like is suitable.

A mixture of the water-absorbent resin precursor and the surface cross-linking agent is heated to be subjected to a cross-linking reaction. Heating temperature may be selected, as appropriate, however, it is preferable that temperature of heating medium be in a range of from 150 to 250° C., more preferably in a range of from 180 to 210° C. In addition, heating time is preferably from 1 minute to 2 hours, and as suitable combination examples of heating temperature and heating time, there are examples of at 180° C. for from 0.1 to 1.5 hour, at 200° C. for from 0.1 to 1 hour and the like.

(11) Granulation

In the present invention, it is preferable that a polymer obtained via multiple times of the surface cross-linking steps (hereinafter may be referred to simply as "a surface cross-linked water-absorbent resin") is granulated. Upon granulation, the mass average particle diameter of water-absorbent resin particles or a water-absorbent agent can be increased (for example, by 1.01 times, preferably by 1.05 to 5 times) and the amount of particles having particle diameters of less than 75 μm such as fine powder can be decreased. In addition, the particles obtained upon granulation (granulated particles) are in the form of two or more primary particles being combined (preferably in the form of a bunch of grapes). Such a form can be confirmed by an observation with an optical microscope or electron microscope.

For the granulation, it is preferable that water and, if necessary, a hydrophilic organic solvent is used, and after mixing these solvents with a surface cross-linked water-absorbent resin, the resultant mixture is heated. Amount of water to be used in the granulation depends on content of water of the surface cross-linked water-absorbent resin to be subjected to the granulation, however, it is usually from 0.5 to 20% by mass, preferably from 0.5 to 10% by mass, relative to 100% by mass of solid content of the surface cross-linked water-absorbent resin. The addition amount of the hydrophilic organic solvent is usually from 0 to 10% by mass, preferably from 0 to 5% by mass, and more preferably from 0 to 3% by mass, relative to 100% by mass of the mixture of the surface cross-linked water-absorbent resin and water. There is an advantage that mixing performance becomes high, and excellent granulated material can be obtained by using the hydrophilic organic solvent. Temperature in the addition of the hydrophilic organic solvent is preferably, in consideration of mixing performance, from 0 to 80° C., and more preferably from 40 to 70° C. In addition, the addition embodiment of the hydrophilic organic solvent is not especially limited, however, a method for spraying or dropping the hydrophilic organic solvent to the mixture of the surface cross-linked water-absorbent resin and water is preferable, and a method for spraying is more preferable. Size of a droplet to be sprayed is preferably from 1 to 300 μm, and more preferably from 1 to 200 μm.

Heating time is preferably within a range of from 1 minute to 2 hours. The addition of water and heating may be carried out by the same apparatus, or by different apparatus. Heating may be carried out under stirring or in standing still (no stirring) as long as temperature and content of water can be controlled, however, it is preferable that curing (into a loose block-like) is carried out in standing still (no stirring). It is preferable that the surface cross-linked water-absorbent resin added with water is cured by lamination in a degree of from 1 to 100 cm, preferably from 5 to 80 cm, and more preferably from 10 to 70 cm, and by heating. The cured surface cross-linked water-absorbent resin is subsequently crushed, and preferably classified further, to obtain a water-absorbent resin composing an objective water-absorbent agent.

(12) Shape of a Water-Absorbent Agent

A water-absorbent agent of the present invention is preferably particulate in view of water absorption characteristics, and it is preferable that mass average particle diameter (D50) is in a range from 200 to 600 μm, more preferably in a range from 200 to 550 μm, and still more preferably in a range from 250 to 500 μm. Lower content of particles, having a size of below a JIS standard sieve 150 μm, is better, and usually the content is from 0 to 5% by mass, preferably from 0 to 3% by mass and particularly preferably from 0 to 1% by mass. Still more, lower content of particles, having a size of equal to or larger than a JIS standard sieve 850 μm, is better, and usually the content is from 0 to 5% by mass, preferably from 0 to 3% by mass and particularly preferably from 0 to 1% by mass. Bulk density thereof (specified in the specification of U.S. Pat. No. 6,562,879) is from 0.30 to 0.90 (g/cm$^3$), preferably from 0.60 to 0.80 (g/cm$^3$), and more preferably from 0.65 to 0.75 (g/cm$^3$).

Shape of a particulate water-absorbent agent is not especially limited, however, there is included spherical shape, nearly spherical shape, irregular and crushed shape (a crushed substance), bar shape, polyhedron shape, sausage shape (example; U.S. Pat. No. 4,973,632), particles with wrinkles (example; U.S. Pat. No. 5,744,564) or the like. They may be primary particles (single particles), granulated particles or a mixture thereof. In addition, the particles may be a foamed porous substance. As preferable shape, a primary particle with irregular and crushed shape or shape of a granulate substance thereof is included, and as particularly preferable shape, a spherical primary particle or shape of a granulated substance thereof is included.

(13) Additives

The particulate water-absorbent agent of the present invention may contain various additives.

For example, it is preferable that the particulate water-absorbent agent of the present invention contains a fluidity providing agent. A method for mixing the fluidity providing agent and a water-absorbent resin may be dry blending before or after surface cross-linking, or the above granulation after dry blending, or a method for adding the fluidity providing agent in breaking into flakes of the water-absorbent agent obtained by granulation.

As the fluidity providing agent, for example, water-insoluble inorganic powder which average particle diameter is equal to or smaller than 100 μm (preferably equal to or smaller than 50 μm) is included. As the water-insoluble inorganic powder, it is not especially limited as long as it is one suppressing close adhesion of water-absorbent agent particles themselves when the water-absorbent agent contacts with aqueous liquid, and improves fluidity of the aqueous liquid. An inorganic-type fine particle of such as bentonite, silicon dioxide, titanium oxide, aluminum oxide is preferable to enhance fluid permeability under load of the water-absorbent agent, in the case where, like the water-absorbent agent of the present invention, absorption capacity without load is increased and gel strength is weakened.

A content ratio of the water-absorbent resin and the fluidity providing agent is preferably from 0.05 to 5% by mass, more preferably from 0.3 to 1.0% by mass, and still more preferably from 0.3 to 1.0% by mass, relative to 100% by mass of the water-absorbent resin. The content of the fluidity providing agent equal to or higher than 0.05% by mass provides suitable diffusion absorption index to be described later, and therefore preferable. In addition, the content of the fluidity providing agent equal to or lower than 5% by mass suppresses lowering of water absorption characteristics of absorbent goods, and therefore preferable.

The particulate water-absorbent agent of the present invention preferably contains water. A content of water may be controlled by the above drying treatment or by adding water after surface cross-linking or granulation. A content of water in the particulate water-absorbent agent is preferably from 0.1 to 15% by mass, more preferably from 1 to 10% by mass, and still more preferably from 2 to 6% by mass, relative to 100% by mass of the water-absorbent resin. The content of water equal to or higher than 0.1% by mass provides excellent water-absorbing rate and impact resistance, and therefore preferable. On the other hand, the content water equal to or lower than 15% by mass is capable of suppressing lowering of absorption capacity. It should be noted that value of the above content of water is defined as drying loss in subjecting the water-absorbent resin to heat treatment at 180° C. for 3 hours.

In addition, it is preferable that the particulate water-absorbent agent of the present invention contains a chelating agent as an additive. By the addition of the chelating agent, a water-absorbent agent excellent in urine deterioration resistance or coloring prevention is obtained.

A used amount of the chelating agent, in particular, an amino polyvalent carboxylic acid in the present invention is usually, as a trace component, from 0.00001 to 10% by mass, preferably from 0.0001 to 1% by mass and more preferably from 0.002 to 0.1% by mass, relative to 100% by mass of the surface cross-linked water-absorbent resin as a main component. The used amount equal to or lower than 10% by mass is economical, because effect comparable to the use can be obtained, and generation of a problem of lowering of absorption amount can be suppressed also. In addition, the used amount equal to or higher than 0.00001% by mass is capable of providing sufficient addition effect.

As the chelating agent to be used, a polymer or a non-polymer chelating agent, preferably a non-polymer chelating agent (for example, one having a molecular weight or a mass average molecular weight of from 40 to 2000, preferably from 60 to 1000, and more preferably from 100 to 500) may be added to a monomer or a polymer thereof. As a preferable chelating agent, an aminocarboxylic acid (a salt thereof) is included, and number of carboxylic acid thereof is preferably from 2 to 20, more preferably from 4 to 10 and still more preferably from 5 to 8.

As the aminocarboxylic acid-type chelating agent, there is exemplified, for example, iminodiacetic acid, hydroxyethyl iminodiacetic acid, nitrilotriacetic acid, nitrilotripropionic acid, ethylenediamine tetraacetic acid, hydroxyethylenediamine triacetic acid, hexamethylenediamine tetraacetic acid, diethylenetriamine pentaacetic acid, triethylene tetramine hexaacetic acid, trans-1,2-diaminocyclohexane tetraacetic acid, bis(2-hydroxyethyl)glycine, diaminopropanol tetraacetic acid, ethylenediamine-dipropionic acid, glycol ether diamine tetraacetic acid, bis(2-hydroxybenzyl)ethylenediamine diacetic acid and a salt thereof or the like.

As a phosphoric acid-type chelating agent, there is exemplified, for example, a phosphorus compound such as ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphonic acid, nitrilotris(methyleneacetic acid), cyclohexanediamine tetra(methylenephosphonic acid), ethylenediamine-N,N'-diacetic acid-N,N'-di(methylenephosphonic acid), ethylenediamine-N,N'-di(methylenephosphonic acid), ethylenediamine tetra(methylenephosphonic acid), polymethylenediamine tetra(phosphonic acid), diethylenetriamine penta(methylenephosphonic acid), 1-hydroroxyethylidenediphosphonic acid, and a salt.

In addition, the water-absorbent agent of the present invention is preferable also in view of exerting durability (urine deterioration prevention) and coloring prevention effect by containing the chelating agent and the fluidity providing agent within the above range.

The particulate water-absorbent agent of the present invention may further contain, if necessary, a deodorant, an antibacterial agent, perfume, a surfactant, fertilizer, an oxidizing agent, a reducing agent, a hydrophilic polymer, a hydrophobic polymer such as paraffin, a thermoplastic resin such as polyethylene, polypropylene, in an amount of preferably from 0 to 20% by mass, more preferably from 0.001 to 10% by mass, relative to 100% by mass of the water-absorbent resin.

(14) Property of the Water-Absorbent Agent

According to other embodiment of the present invention, a novel particulate water-absorbent agent can be provided as well. That is, the present invention provides a particulate water-absorbent agent having a polyacrylate salt-type water-absorbent resin as a main component, and having an absorption capacity without load of equal to or higher than 28 g/g, characterized by satisfying the following (a) to (c):

(a) amount of water-soluble component under stirring is from 15 to 60% by mass;
(b) difference between an amount of water-soluble component under stirring and an amount of water-soluble component in standing still (amount of water-soluble component under stirring−amount of water-soluble component in standing still) is from 15 to 50% by mass; and
(c) diffusion absorption index is from 1.40 to 10.0 g/g/min;
wherein the amount of water-soluble component under stirring represents amount of a dissolution polymer, after 16 hours, to a normal saline solution under stirring, and the amount of water-soluble component in standing still represents amount of a dissolution polymer, after 16 hours, to a normal saline solution in standing still.

A water-absorbent agent satisfying the above properties suppresses lowering of absorption capacity after elapse of a long time, and reduces Re-wet. And, even when this water-absorbent agent is used in absorbent goods in a high content state thereof, there are advantages that aqueous liquid added in a large amount at one time can be absorbed and diffused quickly, and absorption characteristics can be maintained, even after elapse of along time, and the aqueous liquid never returns.

Referring to (a), an amount of water-soluble component under stirring of the particulate water-absorbent agent of the present invention is from 15 to 60% by mass, preferably 18 to 50% by mass, still more preferably 20 to 40% by mass, and particularly preferably 22 to 35% by mass. The amount of water-soluble component under stirring below 15% by mass or the amount of water-soluble component under stirring over 60% by mass could lower absorption capacity of the water-absorbent agent after elapse of a long time.

In addition, referring to (b), a value of (amount of water-soluble component under stirring−amount of water-soluble component in standing still) of the particulate water-absorbent agent of the present invention is from 15 to 50% by mass, preferably 20 to 50% by mass, and more preferably 25 to 50% by mass. This value below 15% by mass could lower absorption capacity of the water-absorbent agent after elapse of a long time. On the other hand, this value over 50% by mass is not realistic. It should be noted that because the amount of water-soluble component in standing still is measured without stirring, it becomes smaller than the amount of water-soluble component under stirring, therefore the value of the above difference becomes always positive value.

As described above, the present inventors have found that conventional improvement directions of a water-absorbent resin (to enhance absorption capacity under load or without load, to reduce amount of water-soluble component, to enhance gel strength and the like), which have been viewed as common sense, provide adverse effect on property of a water-absorbent agent (water-absorbent resin) used in disposable diapers on the premise of use for a long time, because of low amount of water-soluble component. And, there has been found that in a water-absorbent agent (water-absorbent resin) for disposable diapers on the premise of use for a long time, with being different from conventional improvement directions, the amount of water-soluble component to be equal to or higher than a certain level is necessary for enhancement of absorption amount in use for a long time. It should be noted that a water-absorbent resin having the amount of water-soluble component under stirring (conventional amount of water-soluble component) of from about 1 to 5% has been known, however, in such a water-absorbent resin, because an amount of water-soluble component in standing still is still more low, the difference becomes from 0 to several % by mass.

Referring to (c), a diffusion absorption index of the particulate water-absorbent agent of the present invention is from 1.40 to 10 g/g/minute, preferably from 2.0 to 10 g/g/minute, and more preferably from 3.0 to 10 g/g/minute. The diffusion absorption index below 1.4 g/g/minute could not provide excellent absorption characteristics, when such a water-absorbent agent is used in absorbent goods. On the other hand, the diffusion absorption index over 10 g/g/minute is not realistic. It should be noted that "diffusion absorption index" is defined as maximal increase amount per 1 minute (g/g/min) of diffusion absorption capacity (g/g) under a load of 1.9 kPa, and an absorption index in a lateral direction against pressure, measured according to the specification of U.S. Pat. No. 5,797,893 or the specification of U.S. Pat. No. 5,760,080.

It is not especially limited on other properties of the particulate water-absorbent agent of the present invention, however, an absorption capacity without load (GV) is preferably equal to or higher than 28 g/g, more preferably equal to or higher than 30 g/g and still more preferably equal to or higher than 33 g/g. The absorption capacity without load below 28 g/g could provide insufficient absorption performance when such a water-absorbent agent is used in absorbent goods such as disposable diapers. It should be noted that higher value of the absorption capacity without load is better, however, in view of balance with other properties or production cost, it is usually equal to or lower than 45 g/g, still more equal to or lower than 40 g/g, and particularly about 38 g/g is enough.

An absorption capacity under load (AAP1.9 kPa), under a pressure (under load) of 1.9 kPa, to a normal saline solution of the water-absorbent agent of the present invention is preferably equal to or higher than 20 g/g, and more preferably equal to or higher than 25 g/g. In addition, the absorption capacity under load (AAP4.8 kPa), under a pressure (under load) of 4.8 kPa, is preferably equal to or higher than 10 g/g, and more preferably equal to or higher than 15 g/g. The case when the absorption capacity under load is low could not fulfill effect of the present invention. It should be noted that the upper limit is preferable as high as possible, however, in view of balance with other properties or production cost, it is equal to or lower than 40 g/g, and particularly equal to or lower than about 35 g/g is enough.

(15) Water-Absorbent Goods

Applications of the water-absorbent agent of the present invention are not especially limited, however, it is preferably used in an absorbent body or absorbent goods.

The absorbent body is obtained by using a water-absorbent agent. Here, the absorbent body means an absorbing substance formed by making a water-absorbent agent and a hydrophilic fiber as main components. In the present invention, content of the water-absorbent agent (core concentration) relative to total mass of the water-absorbent agent and the hydrophilic fiber, is not especially limited, however, it is preferably from 40 to 100% by mass, more preferably from 50 to 90% by mass, and particularly preferably from 60 to 80% by mass.

Because the water-absorbent agent of the present invention has good fluid permeability, in the case where this is used in the absorbent body, good fluid diffusion performance is secured, even when content of the hydrophilic fiber is reduced, and content of the water-absorbent agent is increased to equal to or higher than 40% by mass. As a result, aqueous liquid added in a large quantity at one time can be absorbed and diffused quickly, and absorption characteristics can be maintained, even after elapse of a long time, and the aqueous liquid never returns again. Therefore, the absorbent body using the water-absorbent agent of the present invention can be made thinner.

The absorbent goods of the present invention is provided with the absorbent body, a surface sheet having fluid permeability, and a back sheet having fluid non-permeability. The water-absorbent agent of the present invention is applicable to other sanitary materials such as incontinence pads.

The absorbent goods of the present invention is capable of quickly absorbing and diffusing aqueous liquid added in a large quantity at one time, and therefore absorption characteristics can be maintained, even after elapse of a long time, and the aqueous liquid never returns again. Because of small amount of Re-wet, and good dry feeling, load of a person wearing the goods, as well as a care-giver, can be reduced.

It is preferable that the absorbent goods of the present invention have a long time absorbing amount, to be described later, of equal to or higher than 270 g. The long time absorbing amount equal to or higher than 270 g provides good fit feeling to a person wearing the goods, and suppresses generation of fluid leakage or rash.

EXAMPLES

Explanation will be given below in detail on the present invention with reference to Examples, however, the technical scope of the present invention should not be limited only to the following Examples. It should be noted that properties of a water-absorbent resin, a particulate water-absorbent agent (a water-absorbent agent) and a water-absorbent goods were measured by the following methods.

(Measurement conditions): 25° C.±2° C., relative humidity of 50% RH (Measurement solution): a normal saline solution, that is, an aqueous solution of 0.90% by mass of sodium chloride (Disposable diapers): In the case where a water-absorbent agent in disposable diapers or the like is in moisture uptake, it is submitted to drying under reduced pressure, as appropriate (for example, drying at from 60 to 80° C. for about 16 hours) till equilibrium of content of water (around 5% bay mass, from 2 to 8% by mass) of the water-absorbent agent is attained, before submitting to property measurement.

It should be noted that a disclosed method using a word "water-absorbent agent" is also applied to water-absorbent resin precursor or water-absorbent resin other than water-absorbent agent as for disclosed method in the below Example column. Therefore, the word "water-absorbent agent" is used unless there is a specific reason in the below disclosure.

(1) Absorption Capacity without Load (GV)

Into a bag (60 mm×60 mm) made of nonwoven fabric (Heatron Paper: Grade GS-22, manufactured by Nangoku Pulp Industry. Co., Ltd.), 0.20 g of a water-absorbent agent was uniformly charged and sealed. Then it was immersed into a normal saline solution for 30 minutes. Then this bag was pulled up and subjected to drainage, by using a centrifugal separator (Type H-122, centrifugal separator, manufactured by KOKUSAN Co., Ltd.) at 250 G for 3 minutes to measure bag mass W1 (g). In addition, the same procedure was carried out without using the water-absorbent agent to measure bag mass W0 (g). Then, using these masses W1 and W0, absorption capacity without load (g/g) was calculated by the following equation:

Absorption capacity without load($GV$) (g/g)=
[($W1$ (g)−$W0$ (g))/mass of a water-absorbent agent (g)]−1

(2) Absorption Capacity Under Load (AAP1.9 kPa)

According to the specification of U.S. Pat. No. 6,071,976, absorption capacity under load (value at 60 minutes) to a normal saline solution against 50 g/cm² (AAP1.9 kPa) was determined.

That is, 0.9 g of a water-absorbent agent was uniformly spread on the bottom of a plastic support cylinder, with an inner diameter of 60 mm, and a load of 1.9 kPa (0.3 psi) per 1 g of the water-absorbent agent was uniformly added thereon to determine absorption amount in 1 hour. Then a set of the measurement apparatus was lifted up to measure mass Wb (g) thereof. Then, using Wa, mass of the set of the measurement apparatus before measurement, and Wb determined above, absorption capacity under load (g/g) was calculated by the following equation:

Absorption capacity under load($AAP$1.9 kPa) (g/g)=
($Wb$ (g)−$Wa$ (g))/mass of a water-absorbent agent (0.90 g)

(3) Absorption Capacity Under Load (AAP4.8 kPa)

Absorption capacity under load (AAP4.8 kPa) was determined in the same manner as in the AAP1.9 kPa except that a load of 4.8 kPa (0.7 psi) was added to a water-absorbent agent.

(4) Mass Average Particle Diameter (D50) and Logarithmic Standard Deviation (σζ)

According to the pamphlet of WO 2005/092956, size distribution and logarithmic standard deviation (σζ) thereof were determined by classifying 10 g of a water-absorbent agent by using a JIS standard sieve. That is, a water-absorbent agent was classified by using standard JIS sieves with mesh opening size of 850 μm, 500 μm, 300 μm, 150 μm, and 106 μm, to plot residual %, R, in logarithmic probability paper. By this procedure, mass average particle diameter (D50) was read. In addition, logarithmic standard deviation (σζ) of the size distribution was calculated by the following equation:

σζ=0.5×ln($X2/X1$)

(wherein X1 and X2 represent particle diameter for R=84.1% by mass and R=15.9% by mass, respectively.)
28p-20L (5) Amount of Water-Soluble Component Under Stirring (Conventional Amount of Water-Soluble Component for 16 Hours: Extr. Under Stirring)

According to the pamphlet of WO 2005/092956, amount of water-soluble component by a conventional method (amount of water-soluble component under stirring) was measured.

That is, in a 250-mL container (Pack Ace, manufactured by Teraoka Co., Ltd.), 184.3 g of a normal saline solution was weighed and charged, and 1.00 g of a water absorbent agent was added thereto, and they were stirred by using a Teflon (registered trade name) stirrer tip (a rod-like one with a length of 35 mm and a diameter and 7 mm) at a stirring rate of 600 rpm for 16 hours to extract water-soluble component in the water-absorbent resin composing the water-absorbent agent. The extracted solution was filtered by using a sheet of filter paper (manufactured by Advantec Toyo Kaisha, Ltd., product name: (JIS P3801, No. 2), with a thickness of 0.26 mm, a retained particle diameter of 5 μm), and 50.0 g of the resultant filtrate was weighed and used as a measurement solution.

First, a normal saline solution alone was titrated with an aqueous 0.1N NaOH solution till pH 10 and subsequently titrated with an aqueous 0.1N HCl solution till pH 2.7 to obtain blank titers (as [bNaOH] ml and [bHCl] ml, respectively).

By carrying out the same titrating operation on the measurement solution, the titers (as [NaOH] ml and [HCl] ml, respectively) were obtained.

For example, in the case of the water-absorbent resin which is composed of known amounts of acrylic acid and a sodium salt thereof, the amount of water-soluble component under stirring in the water-absorbent agent can be calculated by the following formula, based on average molecular weight of the monomer and the titer obtained from the above operation. When the amounts were unknown, average molecular weight of the monomer was calculated by using the neutralization ratio determined by the titration. It should be noted that in the case of a water-absorbent resin not containing an acid group, it is calculated by mass of the filtrate.

Amount of water-soluble component under stirring(% by mass)=0.1×(average molecular weight)×184.3×100×([HCl]−[$b$HCl])/1000/1.0/50.0

Neutralization ratio(% by mole)=[1−([NaOH]−[$b$NaOH])/([HCl]−[$b$HCl])]×100

(6) Amount of Water-Soluble Component in Standing Still (Extr. in Standing Still)

Amount of water-soluble component in standing still was determined in the same manner as in the amount of water-soluble component under stirring, except that 1.00 g of a water-absorbent agent was added into a normal saline solution, which was then stood still without stirring.

(7) Diffusion Absorption Index

Figure 2:
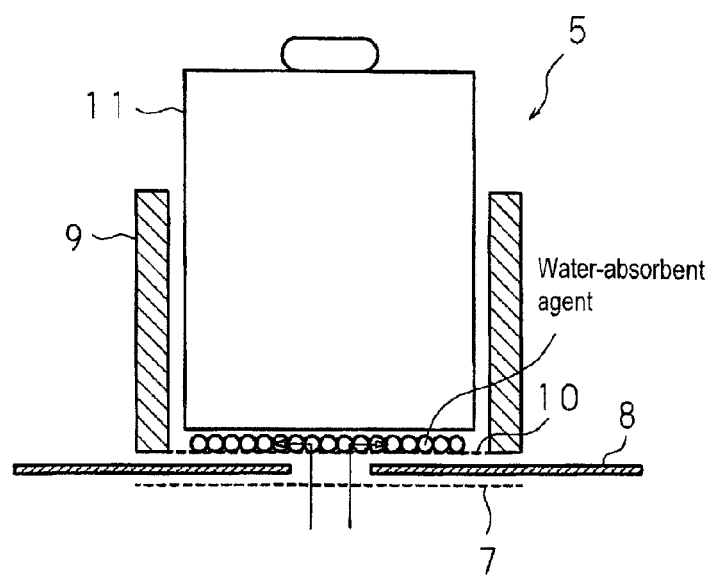
FIG. 2 is a cross-sectional view showing important parts of the measurement apparatus shown in FIG. 1.
Figure 3:
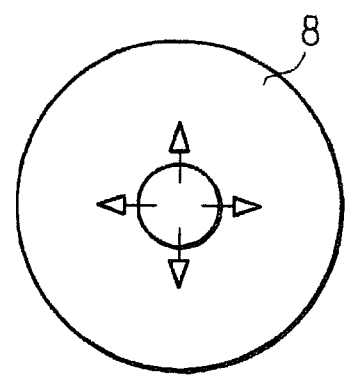
FIG. 3 is a drawing for explaining a diffusion direction of a normal saline solution in the measurement apparatus shown in FIG. 1.

According to the specification of the above U.S. Pat. No. 5,797,893, diffusion absorption index, under a load of 20 g/cm³ (1.96 kPa), was determined by using an apparatus shown in FIGS. 1 to 3. FIG. 1 is a schematic cross-sectional view showing a measurement apparatus used in measurement of diffusion absorption index of a water-absorbent agent of the present invention. FIG. 2 is a cross-sectional view showing important parts of the measurement apparatus. FIG. 3 is a drawing for explaining a diffusion direction of a normal saline solution in the measurement apparatus. Explanation will be given below on measurement method therefor.

First, predetermined preliminary operations were carried out such as predetermined amount of a normal saline solution 12 is charged into a container 2 of FIG. 1; and an outside air suction pipe 3 is fitted to the container 2 and the like. Then, filter paper 7 is put on a glass filter 6, and a sheet 8 was put on this filter paper 7 so that the opening thereof is positioned at the center part of the glass filter 6. On the other hand, along with these putting operations, 1.5 g of a water-absorbent agent was uniformly spread inside a support cylinder 9, that is, on a wire mesh 10, and a weight 11 was put on this water-absorbent agent.

Then, on the sheet 8 of FIG. 2, the wire mesh 10, that is, the support cylinder 9 put with the water-absorbent agent and the weight 11, was put so that the center part thereof coincided with the center part of the glass filter 6.

Subsequently, mass (g) of the normal saline solution 12, which was absorbed by the water-absorbent agent over 60 minutes, from the time when the support cylinder 9 was put on the sheet 8, was measured by using a balance 1. It should be noted that, as shown in FIGS. 2 and 3, the normal saline solution 12 was absorbed into the water-absorbent agent, after passing the opening part of the sheet 8 while nearly uniformly diffusing in a lateral direction (represented by an arrow mark in these FIGS.) of the water-absorbent agent.

Diffusion absorption index was determined by measuring the mass of the normal saline solution 12 absorbed by the water-absorbent agent over 60 minutes, with time, from the time when the support cylinder 9 was put on the sheet 8, by using the measurement apparatus and the balance 1. That is, by using the balance 1, mass of the normal saline solution 12 was measured in a unit of minute, preferably in a unit of second, and from these measurement results, maximal absorption amount per 1 minute was determined, and that value was used as diffusion absorption index (g/g/min).

(8) Long Time Absorption Amount (Performance Evaluation of the Water-Absorbent Goods: a Kewpie Doll Test)

According to the specification of the above U.S. Pat. No. 5,797,893, a water-absorbent agent and wood crushed pulp were blended uniformly, and formed into a web with a size of 120 mm×400 mm. It should be noted that, although a core concentration in said literature was 50% by mass, the core concentration in the present Example was set higher to be 65% by mass (65% by mass of the water-absorbent agent and 35% by mass of the wood crushed pulp). Still more, by pressing this web under a pressure of 2 kg/cm² for 5 seconds, an absorbing body sheet having a basis weight of about 0.047 g/cm² was obtained. By using a disposable diaper prepared by using this absorbent body sheet, the Kewpie doll test was carried out.

It should be noted that the absorbent goods (the disposable diaper) was obtained by adhering a back sheet (fluid non-permeable sheet) composed of fluid non-permeable polypropylene and having, what is called, a leg gathering, the absorbent body sheet, and a top sheet (fluid permeable sheet) composed of fluid permeable polypropylene, each other in this order, by using a both side adhesive tape, and also by fitting two, what is called, tape fasteners onto this adhered substance.

The disposable diaper was fitted to, what is called, a Kewpie doll (body length of 55 cm, and a mass of 5 kg), in the same manner as in the above literature, and after laying this doll in a face-down state, a tube was inserted between the absorbent goods and the doll to sequentially inject 50 g of a normal saline solution per one time, by four times in an interval of 20 minutes, to a position corresponding to a position from where urination is carried out in a human body.

Then, in a measurement method of the above literature, the fifth time injection was carried out after 16 hours of the fourth time injection. At the sixth time injection and hereinafter, injection was carried out in an interval of 20 minutes again.

The injection operation was stopped at the time when the normal saline solution became not absorbed into the absorbent goods and leaked outside, and total amount (g) of the normal saline solution injected up to this time was measured.

The measurement was repeated 4 times, and average of the resultant 4 measurement values was determined, which was used as absorption amount (g). Higher absorption amount was evaluated as better performance of the absorbent goods.

(9) Disposal Test

Swelled gel after use in the above (8) was disposed outdoors to confirm gel shape. Evaluation criteria are as follows:
○: the case where gel was dissolved and disappeared.
Δ: the case where gel maintained the shape as it is.
x: the case where disposal was difficult.

(10) Water Content and Solid Content

On an aluminum dish with the bottom diameter of 50 mm, 1.00 g of a water-absorbent agent was weighed and the total mass W2 (g) of the water-absorbent agent and the aluminum cup was measured. Then, the aluminum cup was left at rest for 3 hours in an oven with the atmospheric temperature of 180° C. to dry the water-absorbent agent. After that, the water-absorbent agent and the aluminum cup taken from the oven were cooled to room temperature in a desiccator and then the total mass after drying W3 (g) was measured, and water content and solid content were calculated in accordance with the following equation.

Water content(% by mass)=($W2-W3$)/(mass of water-absorbent agent (g))×100

Solid content(% by mass)=100−water content

Example 1

Into 5,500 g of 33% by mass aqueous solution of sodium acrylate with a neutralization ratio of 75% by mole, 3.92 g of polyethylene glycol diacrylate (an average addition mole number of ethylene oxide of 8), as an internal cross-linking agent, was dissolved to prepare a reaction solution. Then this reaction solution was subjected to de-airing under nitrogen gas atmosphere for 30 minutes. Then, into a reactor formed by attachment of a cover onto a 10-L (inner volume) stainless double arm-type kneader, equipped with a jacket and two sigma-type blades, the above reaction solution was supplied, and the system was subjected to purging with nitrogen gas while maintaining the reaction solution at 25° C.

Subsequently, under stirring the reaction solution, 2.4 g of sodium persulfate as a polymerization initiator, and 0.012 g of L-ascorbic acid were added, resulting in initiation of polymerization after about 1 minute. Then, polymerization was carried out at from 25 to 95° C., and the reaction was terminated at 40 minutes after initiation of polymerization to yield a water-containing gel-like cross-linked polymer (1), which was finely granulated to about 1 to 5 mm. This finely granulated water-containing gel-like cross-linked polymer (1) was spread on a JIS-300 μm mesh and subjected to hot-air drying at 170° C. for 70 minutes. Then the dried substance was crushed by using a vibration mill, then subjected to classification to yield a polyacrylate salt-type water-absorbent resin precursor (1) in an irregular crushed state.

To 100 parts by mass of the resultant water-absorbent resin precursor (1), an aqueous solution of a surface cross-linking agent, composed of 0.33 part by mass of propylene glycol, 0.21 part by mass of 1,4-butanediol, 0.03 part by mass of ethylene glycol diglycidyl ether, and 1 part by mass of water, was mixed. The mixture was subjected to heat treatment at an oil bath temperature of 203° C. for 30 minutes to yield a surface cross-linked water-absorbent resin precursor (1).

To 100 parts by mass of the resultant surface cross-linked water-absorbent resin precursor (1), an aqueous solution of a surface cross-linking agent, composed of 0.22 part by mass of propylene glycol, 0.14 part by mass of 1,4-butanediol, 4 parts by mass of water, was mixed. This mixture was subjected to heat treatment at an oil bath temperature of 203° C. for 35 minutes to yield a surface cross-linked water-absorbent resin (1).

To 100 parts by mass of the resultant surface cross-linked water-absorbent resin (1), 0.3 part by mass of fine particulate silicon dioxide (commercial name: Aerosil (registered trade name) 200, manufactured by Japan Aerosil Co., Ltd.) as fluidity providing agent was added and mixed to yield a water-absorbent agent (1).

Example 2

Into 5,500 g of 33% by mass aqueous solution of sodium acrylate with a neutralization ratio of 75% by mole, 3.43 g of polyethylene glycol diacrylate (an average addition mole number of ethylene oxide of 8), as an internal cross-linking agent, was dissolved to prepare a reaction solution. Then this reaction solution was subjected to de-airing under nitrogen gas atmosphere for 30 minutes. Then into a reactor formed by attachment of a cover onto a 10-L (inner volume) stainless double arm-type kneader, equipped with a jacket and two sigma-type blades, the reaction solution was supplied, and the system was subjected to purging with nitrogen gas while maintaining the reaction solution at 25° C.

Subsequently, under stirring of the reaction solution, 2.4 g of sodium persulfate and 0.012 g of L-ascorbic acid, as polymerization initiators, were added, resulting in initiation of polymerization after about 1 minute. Then, polymerization was carried out at from 25 to 95° C., and the reaction was terminated 40 minutes after initiation of polymerization to take-out a water-containing gel-like polymer. The resultant water-containing gel-like cross-linked polymer (2) was one finely granulated to about 5 mm. This finely granulated water-containing gel-like cross-linked polymer (2) was spread on a wire mesh with mesh opening size of 300 μm and subjected to hot-air drying at 170° C. for 70 minutes. Then the dried substance was crushed by using a vibration mill, then subjected to classification to yield a water-absorbent resin precursor (2) in an irregular, crushed state.

To 100 parts by mass of the resultant water-absorbent resin precursor (2), an aqueous solution of a surface cross-linking agent, composed of 0.33 part by mass of propylene glycol, 0.21 part by mass of 1,4-butanediol, 0.03 part by mass of ethylene glycol diglycidyl ether, and 1 part by mass of water, was mixed. The mixture was subjected to heat treatment at an oil bath temperature of 203° C. for 30 minutes to yield a surface cross-linked water-absorbent resin precursor (2).

To 100 parts by mass of the resultant surface cross-linked water-absorbent resin precursor (2), an aqueous solution of a surface cross-linking agent, composed of 0.22 part by mass of propylene glycol, 0.14 part by mass of 1,4-butanediol, 4 parts by mass of water, was mixed. The mixture was subjected to heat treatment at an oil bath temperature of 203° C. for 35 minutes to yield a surface cross-linked water-absorbent resin (2).

To 100 parts by mass of the resultant surface cross-linked water-absorbent resin (2), 2 part by mass of an aqueous solution of diethylenetriamine pentaacetic acid as chelating agent was added so that diethylenetriamine pentaacetic acid sodium salt was 100 ppm by mass to the water-absorbent resin. Further 0.3 part by mass of fine particulate silicon dioxide (commercial name: Aerosil (registered trade name) 200, manufactured by Japan Aerosil Co., Ltd.) was added and mixed to yield a water-absorbent agent (2).

Example 3

Into a 2-L four-necked separable flask equipped with a stirrer, a reflux condenser, a thermometer, a nitrogen gas introduction tube and a dropping funnel, 1.0 L of cyclohexane was charged, and 3.8 g of sucrose fatty acid ester (DK-ester F-50, HLB=6, manufactured by Daiichi Kogyo Yakuhin Co., Ltd.), as a dispersing agent, was added and dissolved, and then dissolved oxygen was purged by blowing into nitrogen gas. Separately, into a flask, 84.6 g of sodium acrylate, which is a neutralized substance of acrylic acid, 21.6 g of acrylic acid, and 0.016 g of N,N'-methylenebisacrylamide were dissolved into 197 g of ion-exchanged water, and still more 0.4 g of hydroxyethyl cellulose (HEC-Daicel EP-850, manufactured by Daicel Chemical Industry Co., Ltd.) was dissolved to prepare an aqueous solution of a monomer, with a monomer concentration of 35% by mass. Into this aqueous solution of a monomer, 0.15 g of potassium persulfate was added and dissolved, and then oxygen dissolved in the aqueous solution was purged by blowing into nitrogen gas. Then, the aqueous solution of a monomer in the flask was added into the separable flask and stirred to disperse thereof. After that, bath temperature was raised to 60° C. to initiate a polymerization reaction, and polymerization was completed by maintaining at this temperature for 2 hours. After completion of polymerization, water was removed outside the system by azeotropic dehydration, from a water-containing gel-like substance.

To the dehydrated water-containing gel-like substance, 0.08 part by mass of ethylene glycol diglycidyl ether, as a surface cross-linking agent, and 0.3 part by mass of water were added, and then surface cross-linking was carried out by maintaining bath temperature at 80° C. for 1 hour. Still more, after the addition of 0.08 part by mass of ethylene glycol diglycidyl ether, as a surface cross-linking agent, and 1 part by mass of water, second time surface cross-linking was carried out by maintaining bath temperature at 80° C. for 1 hour. After that, by granulation under reversed-phase suspension (organic solvent: cyclohexane), and subsequent filtration, and drying under reduced pressure at 80° C., a water-absorbent agent (3) was obtained.

Example 4

Into a 2-L four-necked separable flask equipped with a stirrer, a reflux condenser, a thermometer, a nitrogen gas introduction tube and a dropping funnel, 1.0 L of cyclohexane was charged, and 3.8 g of sucrose fatty acid ester (DK-ester F-50, HLB=6, manufactured by Daiichi Kogyo Yakuhin Co., Ltd.), as a dispersing agent, was added and dissolved, and then dissolved oxygen was purged by blowing into nitrogen gas. Separately, into a flask, 84.6 g of sodium acrylate, as a neutralized substance of acrylic acid, 21.6 g of acrylic acid, and 0.016 g of N,N'-methylenebisacrylamide were dissolved into 197 g of ion-exchanged water, and still more 0.4 g of hydroxyethyl cellulose (HEC-Daicel EP-850, manufactured by Daicel Chemical Industry Co., Ltd.) was dissolved to prepare an aqueous solution of a monomer, with a monomer concentration of 35% by mass. Into this aqueous solution of a monomer, 0.15 g of potassium persulfate was added and dissolved, and then oxygen dissolved in the aqueous solution was purged by blowing into nitrogen gas. Then, the aqueous solution of a monomer in the flask was added into the separable flask and stirred to disperse thereof. After that, bath temperature was raised to 60° C. to initiate a polymerization reaction, and polymerization was completed by maintaining at this temperature for 2 hours. After completion of polymerization, by filtration and air-drying in a draft chamber for about 1 hour, a water-containing gel-like substance was taken out.

To the water-containing gel-like substance, 0.08 part by mass of ethylene glycol diglycidyl ether, as a surface cross-linking agent, and 0.3 part by mass of water were added, and then surface cross-linking was carried out by maintaining bath temperature at 80° C. for 1 hour. Then, filtration was carried out after granulation under reversed-phase suspension (organic solvent: cyclohexane), and the resultant granulated substance was dried under reduced pressure at 80° C. (content of water: 10% by mass). Still more, after the addition again of 0.03 part by mass of ethylene glycol diglycidyl ether, as a surface cross-linking agent, 0.5 part by mass of propylene glycol and 1 part by mass of water, second time surface cross-linking was carried out by holding the dried granulated substance in an oven at a temperature at 150° C. for 30 minutes to yield a water-absorbent agent (4).

Example 5

Into 5,500 g of 33% by mass aqueous solution of sodium acrylate with a neutralization ratio of 75% by mole, 14.84 g of polyethylene glycol diacrylate (an average addition mole number of ethylene oxide of 8), as an internal cross-linking agent, and 0.41 g of sodium hypophosphite as a chain transfer agent were dissolved to prepare a reaction solution. Then this reaction solution was subjected to de-airing under nitrogen gas atmosphere for 30 minutes. Then, into a reactor formed by attachment of a cover onto a 10-L (inner volume) stainless double arm-type kneader, equipped with a jacket and two sigma-type blades, the above reaction solution was supplied, and the system was subjected to purging with nitrogen gas while maintaining the reaction solution at 25° C.

Subsequently, under stirring the reaction solution, 2.4 g of sodium persulfate as a polymerization initiator, and 0.012 g of L-ascorbic acid were added, resulting in initiation of polymerization after about 1 minute. Then, polymerization was carried out at from 25 to 95° C., and the reaction was terminated at 40 minutes after initiation of polymerization to yield a water-containing gel-like cross-linked polymer (5), which was finely granulated to about 1 to 5 mm. This finely granulated water-containing gel-like cross-linked polymer (1) was spread on a JIS-300 μm mesh and subjected to hot-air drying at 200° C. for 120 minutes. Then the dried substance was crushed by using a vibration mill, then subjected to classification to yield a polyacrylate salt-type water-absorbent resin precursor (5) in an irregular crushed state.

To 100 parts by mass of the resultant water-absorbent resin precursor (5), an aqueous solution of a surface cross-linking agent, composed of 0.33 part by mass of propylene glycol, 0.21 part by mass of 1,4-butanediol, 0.03 part by mass of ethylene glycol diglycidyl ether, and 1 part by mass of water, was mixed. The mixture was subjected to heat treatment at an oil bath temperature of 203° C. for 30 minutes to yield a surface cross-linked water-absorbent resin precursor (5).

To 100 parts by mass of the resultant surface cross-linked water-absorbent resin precursor (5), an aqueous solution of a surface cross-linking agent, composed of 0.22 part by mass of propylene glycol, 0.14 part by mass of 1,4-butanediol, 4 parts by mass of water, was mixed. This mixture was subjected to heat treatment at an oil bath temperature of 203° C. for 35 minutes, and an aqueous solution of a surface cross-linking agent, composed of 0.91 part by mass of 50% aqueous solution of aluminum sulfate, 0.27 part by mass of 60% aqueous solution of sodium lactate, and 0.02 part by mass of propylene glycol was mixed with the mixture and the resultant mixture was subjected to heat treatment at 60° C. for 60 minutes to yield a surface cross-linked water-absorbent resin (5).

To 100 parts by mass of the resultant surface cross-linked water-absorbent resin (5), 0.3 part by mass of fine particulate silicon dioxide (commercial name: Aerosil (registered trade name) 200, manufactured by Japan Aerosil Co., Ltd.) was added and mixed to yield a water-absorbent agent (5).

Example 6

To 100 parts by mass of the surface cross-linked water-absorbent resin (1) obtained in the Example 1 above, an aqueous solution of a surface cross-linking agent, composed of 0.91 part by mass of 50% aqueous solution of aluminum sulfate, 0.27 part by mass of 60% aqueous solution of sodium lactate, and 0.02 part by mass of propylene glycol was mixed and the resultant mixture was subjected to heat treatment at 60° C. for 60 minutes to yield a surface cross-linked water-absorbent resin (6).

To 100 parts by mass of the resultant surface cross-linked water-absorbent resin (6), 0.3 part by mass of fine particulate silicon dioxide (commercial name: Aerosil (registered trade name) 200, manufactured by Japan Aerosil Co., Ltd.) as fluidity providing agent was added and mixed to yield a water-absorbent agent (6).

Comparative Example 1

To 100 parts by mass of the resultant surface cross-linked water-absorbent resin precursor (1) in Example 1, 0.3 part by mass of fine particulate silicon dioxide (commercial name: Aerosil (registered trade name) 200, manufactured by Japan Aerosil Co., Ltd.) was added and mixed to yield a comparative water-absorbent agent (1).

Comparative Example 2

To 100 parts by mass of the resultant surface cross-linked water-absorbent resin precursor (2) in Example 2, 0.3 part by mass of fine particulate silicon dioxide (commercial name: Aerosil (registered trade name) 200, manufactured by Japan Aerosil Co., Ltd.) was added and mixed to yield a comparative water-absorbent agent (2).

Comparative Example 3

Example 5, which provided highest diffusion absorption index, in Examples of U.S. Pat. No. 5,797,893, was carried out as it is.

That is, according to the Example 5 in the literature, Into 5,500 g of 30% by mass aqueous solution of sodium acrylate with a neutralization ratio of 65% by mole, 18.49 g of polyethylene glycol diacrylate (an average addition mole number of ethylene oxide of 8) of an internal cross-linking agent, was dissolved, and by similarly stirring in a stainless double arm-type kneader, polymerization was carried out at from 25 to 95° C. for 60 minutes, and drying and crushing were carried out similarly to yield a water-absorbent resin precursor (3).

Subsequently, according to Example 5 in the literature, to 100 parts by mass of the resultant water-absorbent resin precursor (3), an aqueous solution of a surface cross-linking agent, composed of 0.5 part by mass of glycerine, 1 part by mass of ethanol, 0.05 part by mass of ethylene glycol diglycidyl ether, and 3 parts by mass of water, was mixed. The mixture was subjected to heat treatment at an oil bath temperature of 195° C. for 30 minutes to yield a surface cross-linked water-absorbent resin precursor (3).

To 100 parts by mass of the resultant surface cross-linked water-absorbent resin precursor (3), an aqueous solution of a surface cross-linking agent, composed of 0.5 part by mass of glycerine, 1 part by mass of ethanol, 0.05 part by mass of ethylene glycol diglycidyl ether, and 3 parts by mass of water, was mixed. This mixture was subjected to heat treatment at an oil bath temperature of 195° C. for 30 minutes to yield a comparative water-absorbent resin (3). This comparative water-absorbent resin (3) (Example 5 of U.S. Pat. No. 5,797,893) was used as a comparative water-absorbent agent (3).

Comparative Example 4

In accordance with Example 2 of U.S. Pat. No. 5,672,633, surface cross-linking was carried out twice. That is, to 100 parts by mass of the water-absorbent resin precursor (1) of the Example 1, an aqueous solution of a surface cross-linking agent, composed of 0.5 part by mass of ethylene carbonate, and 0.5 part by mass of water, was mixed. The mixture was subjected to heat treatment at an oil bath temperature of 203° C. for 30 minutes to yield a surface cross-linked water-absorbent resin precursor (4).

To 100 parts by mass of the resultant surface cross-linked water-absorbent resin precursor (4), an aqueous solution of a surface cross-linking agent, composed of 0.2 part by mass of glycerine, 1.2 part by mass of ethanol, and 1 part by mass of water, was mixed. This mixture was subjected to heat treatment at an oil bath temperature of 203° C. for 35 minutes to yield a surface cross-linked water-absorbent resin (4).

Then, inorganic fine particles, not disclosed in the specification of U.S. Pat. No. 5,672,633, were added. That is, to 100 parts by mass of the surface cross-linked water-absorbent resin (4), 2 part by mass of an aqueous solution of diethylenetriamine pentaacetic acid was added so that diethylenetriamine pentaacetic acid sodium salt was 100 ppm by mass to the surface cross-linked water-absorbent resin (4). Further, 0.3 part by mass of fine particulate silicon dioxide (commercial name: Aerosil (registered trade name) 200, manufactured by Japan Aerosil Co., Ltd.) was added and mixed to yield a comparative water-absorbent agent (4).

Analysis results of the resultant particulate water-absorbent agents in the Examples and Comparative Examples are shown in the following Table 1.

In comparisons between Example 1, where the surface cross-linked water-absorbent resin precursor (1) was further subjected to surface cross-linking treatment, and Comparative Example 1, and between Example 2, where the surface cross-linked water-absorbent resin precursor (2) was further subjected to surface cross-linking treatment, and Comparative Example 2, water-absorbent agents (1) and (2) having (b) a difference between amount of water-soluble component under stirring and amount of water-soluble component in standing still (amount of water-soluble component under stirring−amount of water-soluble component in standing still) of from 15 to 50% by mass, and (c) a diffusion absorption index of from 1.40 to 10 g/g/min, provide good disposable diapers having a long time absorption amount of 275 g.

In addition, also in Example 3, where a polymerization method was changed to reversed phase suspension polymerization (shape of a granulated substance of spherical shape (bunch of grapes)), excellent result was obtained not different from Examples 1 and 2, and also excellent performance result that logarithmic standard deviation ($\sigma\zeta$) of size distribution is small, is obtained.

Still more, also in Example 4, where content of water in the surface cross-linking agent in the first time of the surface cross-linking was set 3 times that in the second time of the surface cross-linking, similarly excellent performance result was obtained.

In addition, a similarly excellent performance result was obtained also in the Example 5, in which a polyvalent metal compound (aluminum sulfate), which is an inorganic cross-linking agent, was used as the surface cross-linking agent for the second surface cross-linking.

Comparative Example 3 corresponds to Example showing the highest diffusion absorption index (4.00) in the specification of U.S. Pat. No. 5,797,893, however, it is inferior to the Examples 1 and 2 in that amount of water-soluble component is as small as 8%, and long time absorption amount of a disposable diaper is 250 g.

In the water-absorbent agent of Comparative Example 4, surface cross-linking treatment was carried out twice in accordance with Example 2 of the specification of U.S. Pat.

TABLE 1

| | | Exp. 1 | Exp. 2 | Exp. 3 | Exp. 4 | Exp. 5 | Com. Exp. 1 | Com. Exp. 2 | Com. Exp. 3 | Com. Exp. 4 |
|---|---|---|---|---|---|---|---|---|---|---|
| GV (g/g) | | 34 | 37 | 31 | 34 | 34 | 40 | 44 | 29 | 40 |
| A (% by mass) | | 21 | 23 | 22 | 30 | 21 | 21 | 23 | 8 | 25 |
| B (% by mass) | | 4 | 5 | 4 | 13 | 4 | 10 | 12 | 3 | 14 |
| A − B (% by mass) | | 17 | 18 | 18 | 17 | 17 | 11 | 11 | 5 | 11 |
| Diff. abs. index (g/g/min) | | 2.41 | 1.52 | 1.8 | 2.60 | 2.50 | 1.0 | 0.81 | 4.00 | 1.35 |
| AAP 1.9 kPa (g/g) | | 29 | 28 | 30 | 29 | 29 | 23 | 22 | 25 | 25 |
| AAP 4.8 kPa (g/g) | | 21 | 18 | 16 | 21 | 21 | 13 | 12 | 24 | 15 |
| Long period a. a (g) | | 275 | 275 | 275 | 275 | 275 | 225 | 250 | 250 | 250 |
| Size dist. | 850 μm | 0.0 | 0.0 | 0.0 | 0.0 | 0.0 | 0.0 | 0.0 | 0.0 | 0.0 |
| (% by mass) | 500 μm | 22.6 | 22.6 | 1.0 | 22.6 | 22.6 | 10.6 | 10.6 | 11.5 | 10.6 |
| | 300 μm | 52.0 | 52.0 | 80.0 | 52.0 | 52.0 | 59.9 | 59.9 | 63.0 | 59.9 |
| | 150 μm | 21.9 | 21.9 | 19.0 | 21.9 | 21.9 | 26.7 | 26.7 | 24.0 | 26.7 |
| | 106 μm | 2.5 | 2.5 | 0.0 | 2.5 | 2.5 | 2.2 | 2.2 | 1.0 | 2.2 |
| | PASS | 0.7 | 0.7 | 0.0 | 0.7 | 0.7 | 0.7 | 0.7 | 0.5 | 0.7 |
| D50 (μm) | | 384 | 384 | 345 | 384 | 384 | 352 | 352 | 360 | 352 |
| $\sigma\zeta$ | | 0.38 | 0.38 | 0 | 0.38 | 0.38 | 0.34 | 0.34 | 0.31 | 0.34 |
| Disposal test | | ○ | ○ | ○ | ○ | ○ | — | — | x | — |

(Note)
Exp.: Example, Comp. Exp.: Comparative Example
A: Extracts under stirring,
B: Extracts in standing still
Diff. abs. index: Diffusion absorption index
Long period a. a: Long period absorption amount
Size dist.: Size distribution No. 5,672,633, and has a diffusion absorption index of 1.35 (g/g/min), however, because content of water of aqueous solutions of the surface cross-linking agent in the first time and the second time surface cross-linking are equal to or less than 2 times, a multi-layer like surface cross-linked layer cannot be formed effectively, and difference between amount of water-soluble component under stirring and amount of water-soluble component in standing still is each 11% by mass, and a the water-absorbent agent of the present invention cannot be obtained, showing inferior evaluation result (long time absorption amount) of the absorbent goods, as compared with Examples 1 and 2.

In addition, the water-absorbent agent of Comparative Example 3 maintains gel shape for a long time even after disposal, which makes disposal difficult (ranked x in the disposal test), while the water-absorbent agent of the present invention dissolves (ranked ○ in the disposal test). In addition, as compared with the water-absorbent agent having low amount of water-soluble component, which is disclosed in the specification of reissue U.S. Pat. No. 32,649, the water-absorbent agent of the present invention has advantage in that it can be produced in short polymerization time, under high polymerization concentration and in low cost.

As described above, it is understood that, in the case where a water-absorbent agent has (b) a difference between amount of water-soluble component under stirring and amount of water-soluble component in standing still of from 15 to 50% by mass, and (c) a diffusion absorption index of from 1.40 to 10 g/g/min, an absorbent goods composed of this water-absorbent agent has a good long time absorption amount of equal to or higher than 270 g. In addition, it was also confirmed that, when an absorbent goods is composed by using this water-absorbent agent, aqueous liquid is absorbed and diffused quickly by the absorbent goods, and the aqueous liquid never returns again.

The present application is based on Japanese Patent Application No. 2007-051878, filed on Mar. 1, 2007, the content of which is hereby incorporated by reference in its entirety into this application.

The invention claimed is:

1. A particulate water-absorbent agent comprising a polyacrylate salt-type water-absorbent resin as a main component, and having an absorption capacity without load of equal to or higher than 28 g/g, characterized by satisfying the following (a) to (c):
   (a) amount of water-soluble component under stirring is from 18 to 50% by mass of the water-absorbent agent;
   (b) difference between an amount of water-soluble component under stirring and an amount of water-soluble component in standing still (amount of water-soluble component under stirring–amount of water-soluble component in standing still) is from 15 to 50% by mass of the water-absorbent agent; and
   (c) diffusion absorption index is from 1.40 to 10.0 g/g/min;
   wherein the amount of water-soluble component under stirring represents amount of a dissolution polymer after 16 hours, to a normal saline solution under stirring, and the amount of water-soluble component in standing still represents amount of a dissolution polymer after 16 hours, to a normal saline solution in standing still.

2. The particulate water-absorbent agent according to claim 1, wherein logarithmic standard deviation ($\sigma\zeta$) of size distribution is from 0 to 0.40.

3. The particulate water-absorbent agent according to claim 1, wherein shape of a particle composing the water-absorbent agent is a shape of a spherical primary particle or a granulated substance thereof.

4. The particulate water-absorbent agent according to claim 1, further comprising a fluidity providing agent.

5. The particulate water-absorbent agent according to claim 1, further comprising a chelating agent.

6. The particulate water-absorbent agent according to claim 1, further comprising a water in an amount of from 0.1 to 15% by mass relative to 100% by mass of the water-absorbent resin.

7. A water-absorbent goods characterized by comprising the particulate water-absorbent agent set forth in claim 1, and a hydrophilic fiber.

8. The particulate water-absorbent agent according to claim 2, wherein shape of a particle composing the water-absorbent agent is a shape of a spherical primary particle or a granulated substance thereof.

9. The particulate water-absorbent agent according to claim 2, further comprising a fluidity providing agent.

10. The particulate water-absorbent agent according to claim 3, further comprising a fluidity providing agent.

11. The particulate water-absorbent agent according to claim 8, further comprising a fluidity providing agent.

12. The particulate water-absorbent agent according to claim 2, further comprising a chelating agent.

13. The particulate water-absorbent agent according to claim 3, further comprising a chelating agent.

14. The particulate water-absorbent agent according to claim 8, further comprising a chelating agent.

15. The particulate water-absorbent agent according to claim 9, further comprising a chelating agent.

16. The water-absorbent goods of claim 7, wherein the water-absorbent goods has a long-term absorbing amount of $\geq 270$ g.

* * * * *